United States Patent
Wehner et al.

(10) Patent No.: US 12,240,883 B2
(45) Date of Patent: Mar. 4, 2025

(54) MAGEA1 SPECIFIC T CELL RECEPTORS AND THEIR USE

(71) Applicant: Medigene Immunotherapies GmbH, Planegg-Martinsried (DE)

(72) Inventors: Carina Wehner, Munich (DE); Manon Weis, Sankt Wolfgang (DE); Silke Raffegerst, Wald (DE); Anja Mösch, Munich (DE)

(73) Assignee: Medigene Immunotherapies GmbH, Planegg-Martrinsried (DE)

( * ) Notice: Subject to any disclaimer, the term of this patent is extended or adjusted under 35 U.S.C. 154(b) by 826 days.

(21) Appl. No.: 17/600,518

(22) PCT Filed: Apr. 1, 2020

(86) PCT No.: PCT/EP2020/059193
§ 371 (c)(1),
(2) Date: Sep. 30, 2021

(87) PCT Pub. No.: WO2020/201318
PCT Pub. Date: Oct. 8, 2020

(65) Prior Publication Data
US 2023/0037552 A1    Feb. 9, 2023

(30) Foreign Application Priority Data
Apr. 4, 2019   (EP) .................... 19167440

(51) Int. Cl.
| | | |
|---|---|---|
| C12N 5/02 | (2006.01) |
| A61K 39/00 | (2006.01) |
| A61P 35/00 | (2006.01) |
| C07K 14/47 | (2006.01) |
| C07K 14/725 | (2006.01) |
| C12N 5/0783 | (2010.01) |
| C12N 15/86 | (2006.01) |

(52) U.S. Cl.
CPC ...... *C07K 14/7051* (2013.01); *A61K 39/4611* (2023.05); *A61K 39/4632* (2023.05); *A61K 39/464486* (2023.05); *A61P 35/00* (2018.01); *C07K 14/4748* (2013.01); *C12N 5/0636* (2013.01); *C12N 15/86* (2013.01); *C07K 2317/565* (2013.01); *C12N 2770/00041* (2013.01)

(58) Field of Classification Search
CPC ........... C07K 14/7051; C07K 14/4748; C07K 2317/565; C07K 2317/34; C07K 16/30; C07K 16/2809; A61K 39/4611; A61K 39/4632; A61K 39/464486; A61K 38/00; A61P 35/00; C12N 5/0636; C12N 15/86; C12N 2770/00041; C12N 2510/00
See application file for complete search history.

(56) References Cited

FOREIGN PATENT DOCUMENTS

| | | |
|---|---|---|
| CN | 106749620 | 5/2017 |
| WO | 2014118236 | 8/2014 |
| WO | 2018104438 | 6/2018 |
| WO | 2018170338 | 9/2018 |

*Primary Examiner* — Chun W Dahle
*Assistant Examiner* — Grace H Lunde
(74) *Attorney, Agent, or Firm* — Mandar A. Joshi; Bozicevic, Field & Francis LLP

(57) ABSTRACT

The present invention relates to an isolated T cell receptor (TCR) specific for a MAGEA1-derived peptide and to a polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

Figure 1:
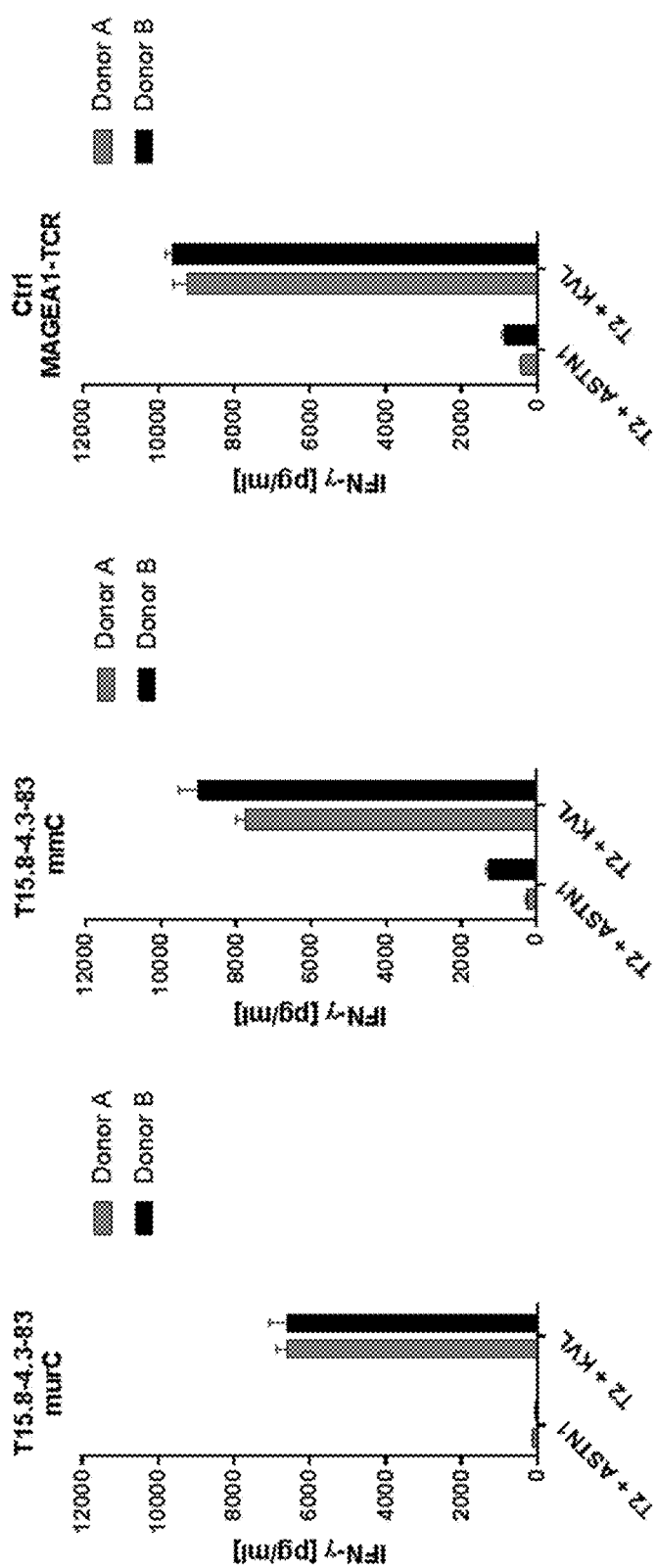

9 Claims, 19 Drawing Sheets
Specification includes a Sequence Listing.

SEQUENCE LISTING

<160> NUMBER OF SEQ ID NOS: 28

<210> SEQ ID NO 1
<211> LENGTH: 9
<212> TYPE: PRT
<213> ORGANISM: Homo sapiens
<400> SEQUENCE: 1

Lys Val Leu Glu Tyr Val Ile Lys Val
1               5

<210> SEQ ID NO 2
<211> LENGTH: 7
<212> TYPE: PRT
<213> ORGANISM: Homo sapiens
<400> SEQUENCE: 2

Thr Arg Asp Thr Thr Tyr Tyr
1               5

<210> SEQ ID NO 3
<211> LENGTH: 8
<212> TYPE: PRT
<213> ORGANISM: Homo sapiens
<400> SEQUENCE: 3

Arg Asn Ser Phe Asp Glu Gln Asn
1               5

<210> SEQ ID NO 4
<211> LENGTH: 15
<212> TYPE: PRT
<213> ORGANISM: Homo sapiens
<400> SEQUENCE: 4

Cys Ala Leu Ser Glu Val Ala Ser Gly Gly Ser Tyr Ile Pro Thr
1               5                   10                  15

<210> SEQ ID NO 5
<211> LENGTH: 6
<212> TYPE: PRT
<213> ORGANISM: Homo sapiens
<400> SEQUENCE: 5

Gly Thr Ser Asn Pro Asn
1               5

<210> SEQ ID NO 6
<211> LENGTH: 5
<212> TYPE: PRT
<213> ORGANISM: Homo sapiens
<400> SEQUENCE: 6

Ser Val Gly Ile Gly
1               5

<210> SEQ ID NO 7
<211> LENGTH: 14
<212> TYPE: PRT
<213> ORGANISM: Homo sapiens
<400> SEQUENCE: 7

Cys Ala Trp Ser Gly Ser Gly Gly Asn Gln Pro Gln His Phe
1               5                   10

<210> SEQ ID NO 8
<211> LENGTH: 138
<212> TYPE: PRT
<213> ORGANISM: Homo sapiens

<400> SEQUENCE: 8

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Val Ala Ser Gly Gly Ser Tyr Ile Pro Thr Phe Gly
        115                 120                 125

Arg Gly Thr Ser Leu Ile Val His Pro Tyr
    130                 135

<210> SEQ ID NO 9
<211> LENGTH: 130
<212> TYPE: PRT
<213> ORGANISM: Homo sapiens

<400> SEQUENCE: 9

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Ser Gly Gly Asn Gln Pro Gln His Phe Gly Asp Gly Thr Arg Leu Ser
        115                 120                 125

Ile Leu
    130

<210> SEQ ID NO 10
<211> LENGTH: 278
<212> TYPE: PRT
<213> ORGANISM: Artificial Sequence
<220> FEATURE:
<223> OTHER INFORMATION: minimal murinized constant region

<400> SEQUENCE: 10

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
        50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Ser Glu Val Ala Ser Gly Gly Ser Tyr Ile Pro Thr Phe Gly
                115                 120                 125

Arg Gly Thr Ser Leu Ile Val His Pro Tyr Ile Gln Asn Pro Asp Pro
            130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
                180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
210                 215                 220

Phe Pro Ser Ser Asp Val Pro Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
        275

<210> SEQ ID NO 11
<211> LENGTH: 307
<212> TYPE: PRT
<213> ORGANISM: Artificial Sequence
<220> FEATURE:
<223> OTHER INFORMATION: minimal murinized constant region

<400> SEQUENCE: 11

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
                20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60

Phe Tyr Ser Val Gly Ile Gly Gln Ile Ser Ser Glu Val Pro Gln Asn
65                  70                  75                  80

```
Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Ser Gly Gly Asn Gln Pro Gln His Phe Gly Asp Gly Thr Arg Leu Ser
        115                 120                 125

Ile Leu Glu Asp Leu Asn Lys Val Phe Pro Pro Glu Val Ala Val Phe
    130                 135                 140

Glu Pro Ser Lys Ala Glu Ile Ala His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305

<210> SEQ ID NO 12
<211> LENGTH: 274
<212> TYPE: PRT
<213> ORGANISM: Artificial Sequence
<220> FEATURE:
<223> OTHER INFORMATION: murine constant region

<400> SEQUENCE: 12

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Val Ala Ser Gly Gly Ser Tyr Ile Pro Thr Phe Gly
        115                 120                 125
```

```
Arg Gly Thr Ser Leu Ile Val His Pro Tyr Ile Gln Asn Pro Glu Pro
            130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Thr Val Leu Asp Met Lys Ala Met
                180                 185                 190

Asp Ser Lys Ser Asn Gly Ala Ile Ala Trp Ser Asn Gln Thr Ser Phe
            195                 200                 205

Thr Cys Gln Asp Ile Phe Lys Glu Thr Asn Ala Thr Tyr Pro Ser Ser
        210                 215                 220

Asp Val Pro Cys Asp Ala Thr Leu Thr Glu Lys Ser Phe Glu Thr Asp
225                 230                 235                 240

Met Asn Leu Asn Phe Gln Asn Leu Ser Val Met Gly Leu Arg Ile Leu
                245                 250                 255

Leu Leu Lys Val Ala Gly Phe Asn Leu Met Thr Leu Arg Leu Trp
            260                 265                 270

Ser Ser

<210> SEQ ID NO 13
<211> LENGTH: 303
<212> TYPE: PRT
<213> ORGANISM: Artificial Sequence
<220> FEATURE:
<223> OTHER INFORMATION: murine constant region

<400> SEQUENCE: 13

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
                20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Ser Gly Gly Asn Gln Pro Gln His Phe Gly Asp Gly Thr Arg Leu Ser
        115                 120                 125

Ile Leu Glu Asp Leu Arg Asn Val Thr Pro Pro Lys Val Thr Leu Phe
130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205
```

```
Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
                260                 265                 270

Ile Leu Tyr Glu Ile Leu Leu Gly Lys Ala Thr Leu Tyr Ala Val Leu
                275                 280                 285

Val Ser Gly Leu Val Leu Met Ala Met Val Lys Lys Lys Asn Ser
    290                 295                 300
```

<210> SEQ ID NO 14
<211> LENGTH: 21
<212> TYPE: DNA
<213> ORGANISM: Artificial Sequence
<220> FEATURE:
<223> OTHER INFORMATION: codon optimized

<400> SEQUENCE: 14
acacgggaca ccacctacta c          21

<210> SEQ ID NO 15
<211> LENGTH: 24
<212> TYPE: DNA
<213> ORGANISM: Artificial Sequence
<220> FEATURE:
<223> OTHER INFORMATION: Codon optimized

<400> SEQUENCE: 15
cggaacagct tcgacgagca gaac          24

<210> SEQ ID NO 16
<211> LENGTH: 45
<212> TYPE: DNA
<213> ORGANISM: Artificial Sequence
<220> FEATURE:
<223> OTHER INFORMATION: Codon optimized

<400> SEQUENCE: 16
tgcgccctga gcgaagtggc cagcggcggc tcttacatcc ctaca          45

<210> SEQ ID NO 17
<211> LENGTH: 18
<212> TYPE: DNA
<213> ORGANISM: Artificial Sequence
<220> FEATURE:
<223> OTHER INFORMATION: Codon optimized

<400> SEQUENCE: 17
ggcaccagca atcccaac          18

<210> SEQ ID NO 18
<211> LENGTH: 15
<212> TYPE: DNA
<213> ORGANISM: Artificial Sequence
<220> FEATURE:
<223> OTHER INFORMATION: Codon optimized

<400> SEQUENCE: 18
agcgtcggca tcggc          15

```
<210> SEQ ID NO 19
<211> LENGTH: 42
<212> TYPE: DNA
<213> ORGANISM: Artificial Sequence
<220> FEATURE:
<223> OTHER INFORMATION: codon optimized

<400> SEQUENCE: 19
tgtgcttgga gtggcagcgg cggcaatcag cctcagcact tt                         42

<210> SEQ ID NO 20
<211> LENGTH: 414
<212> TYPE: DNA
<213> ORGANISM: Artificial Sequence
<220> FEATURE:
<223> OTHER INFORMATION: Codon optimized

<400> SEQUENCE: 20
atgctgacag cctctctgct gagagccgtg atcgccagca tctgtgtggt gtctagcatg      60
gcccagaaag tgacacaggc ccagaccgag atcagcgtgg tggaaaaaga agatgtgacc     120
ctggactgcg tgtacgagac acgggacacc acctactacc tgttctggta caagcagcct    180
cctagcggcg agctggtgtt cctgatcaga cggaacagct cgacgagca gaacgagatc     240 tccggccggt acagctggaa cttccagaag tccaccagca gcttcaactt caccatcacc    300
gccagccagg tggtggatag cgccgtgtat ttttgcgccc tgagcgaagt ggccagcggc    360
ggctcttaca tccctacatt tggcagaggc accagcctga tcgtgcaccc ttat           414

<210> SEQ ID NO 21
<211> LENGTH: 390
<212> TYPE: DNA
<213> ORGANISM: Artificial Sequence
<220> FEATURE:
<223> OTHER INFORMATION: codon optimized

<400> SEQUENCE: 21
atgctgtgtt ctctgctggc tctgctgctg ggcacctttt ttggcgtcag aagccagacc      60
atccaccagt ggcctgctac actggtgcag cctgttggaa gccctctgag cctggaatgt    120
accgtggaag gcaccagcaa tcccaacctg tactggtaca gacaggccgc tggaagagga    180
ctgcagctgc tgttttacag cgtcggcatc ggccagatca gcagcgaggt tccacagaat    240
ctgagcgcca gcagacccca ggacagacag tttatcctga gcagcaagaa gctgctgctg    300
agcgacagcg gcttctacct gtgtgcttgg agtggcagcg gcggcaatca gcctcagcac    360
tttggagatg gcacccggct gagcatcctg                                       390

<210> SEQ ID NO 22
<211> LENGTH: 837
<212> TYPE: DNA
<213> ORGANISM: Artificial Sequence
<220> FEATURE:
<223> OTHER INFORMATION: minimal murinized constat region, codon
      optimized

<400> SEQUENCE: 22
atgctgacag cctctctgct gagagccgtg atcgccagca tctgtgtggt gtctagcatg      60
gcccagaaag tgacacaggc ccagaccgag atcagcgtgg tggaaaaaga agatgtgacc     120
ctggactgcg tgtacgagac acgggacacc acctactacc tgttctggta caagcagcct    180
cctagcggcg agctggtgtt cctgatcaga cggaacagct cgacgagca gaacgagatc     240 tccggccggt acagctggaa cttccagaag tccaccagca gcttcaactt caccatcacc    300
```

```
gccagccagg tggtggatag cgccgtgtat ttttgcgccc tgagcgaagt ggccagcggc    360
ggctcttaca tccctacatt tggcagaggc accagcctga tcgtgcaccc ttatattcag    420
aaccccgatc ctgccgtgta ccagctgaga cagcaagaa gcagcgacaa gagcgtgtgt    480
ctgttcaccg acttcgacag ccagaccaac gtgtcccaga gcaaggacag cgacgtgtac    540
atcaccgaca gaccgtgct ggacatgcgg agcatggact tcaagagcaa cagcgccgtg     600
gcctggtcca acaagagcga tttcgcctgc gccaacgcct tcaacaatag cattatcccc    660
gaggacacat tcttccccag ctccgatgtg ccctgcgacg tgaagctggt ggaaaagagc    720
ttcgagacac acaccaacct gaacttccag aacctgagcg tgatcggctt cagaatcctg    780
ctgctgaagg tggccggctt caatctgctg atgaccctga ctgtgggtc cagctga       837

<210> SEQ ID NO 23
<211> LENGTH: 924
<212> TYPE: DNA
<213> ORGANISM: Artificial Sequence
<220> FEATURE:
<223> OTHER INFORMATION: minimal murinized constant region, codon
      optimized

<400> SEQUENCE: 23
atgctgtgtt ctctgctggc tctgctgctg ggcacctttt ttggcgtcag aagccagacc     60
atccaccagt ggcctgctac actggtgcag cctgttggaa ccctctgag cctggaatgt    120 accgtggaag gcaccagcaa tcccaacctg tactggtaca gcaggccgc tggaagagga    180 ctgcagctgc tgttttacag cgtcggcatc ggccagatca gcagcgaggt tccacagaat    240
ctgagcgcca gcagacccca ggacagacag tttatcctga gcagcaagaa gctgctgctg    300
agcgacagcg gcttctacct gtgtgcttgg agtggcagcg cggcaatca gcctcagcac    360 tttggagatg gcacccggct gagcatcctg aagatctga acaaggtgtt ccctccagag    420
gtggccgtgt tcgagccttc taaggccgag attgcccaca cacagaaagc cacactcgtg    480
tgcctggcta ccggcttctt tcctgaccac gtggaactgt cttggtgggt caacggcaaa    540
gaggtgcaca cgcgcgtcag cacagatccc agcctctga aagaacagcc cgctctgaac    600
gacagccggt actgtctgag cagcagactg agagtgtccg ccacattctg gcagaacccc    660
agaaaccact tcagatgcca ggtgcagttc tacggcctga gcgagaacga tgagtggacc    720
caggatagag ccaagcctgt gacacagatc gtgtctgccg aagcctgggg cagagccgat    780
tgtggaatta ccagcgccag ctaccatcag gcgtgctgt ctgccacaat cctgtacgag    840
atcctgctgg gcaaagccac tctgtacgcc gtgctggtgt ctgccctggt gctgatggcc    900
atggtcaaga gaaaggactt ttga                                         924

<210> SEQ ID NO 24
<211> LENGTH: 825
<212> TYPE: DNA
<213> ORGANISM: Artificial Sequence
<220> FEATURE:
<223> OTHER INFORMATION: murine constant region, codon optimized

<400> SEQUENCE: 24
atgctgacag cctctctgct gagagccgtg atcgccagca tctgtgtggt gtctagcatg     60
gcccagaaag tgacacaggc ccagaccgag atcagcgtgg tggaaaaaga agatgtgacc    120
ctggactgcg tgtacgagac acgggacacc acctactacc tgttctgta caagcagcct    180 cctagcggcg agctggtgtt cctgatcaga cggaacagct tcgacgagca gaacgagatc    240
```

```
tccggccggt acagctggaa cttccagaag tccaccagca gcttcaactt caccatcacc      300
gccagccagg tggtggatag cgccgtgtat ttttgcgccc tgagcgaagt ggccagcggc      360
ggctcttaca tccctacatt tggcagaggc accagcctga tcgtgcaccc ttatatccag      420
aatccggagc cgccgtgtat ccagctgaag gaccctagaa gccaggacag caccctgtgc      480
ctgttcaccg acttcgacag ccagatcaac gtgcccaaga ccatggaaag cggcaccttc      540
atcaccgaca gacagtgct ggacatgaag gccatggaca gcaagtccaa cggcgcaatc       600
gcctggtcca accagaccag cttcacatgc caggacatct tcaaagagac aaacgccaca      660 tacccccagca gcgacgtgcc ctgtgatgcc accctgacag agaagtcctt cgagacagac     720
atgaacctga acttccagaa tctgtccgtg atgggcctga aatcctgct gctgaaggtg       780 gccggcttca atctgctgat gaccctgcgg ctgtggtcca gctga                      825

<210> SEQ ID NO 25
<211> LENGTH: 912
<212> TYPE: DNA
<213> ORGANISM: Artificial Sequence
<220> FEATURE:
<223> OTHER INFORMATION: murine constant region

<400> SEQUENCE: 25
atgctgtgtt ctctgctggc tctgctgctg ggcacctttt ttggcgtcag aagccagacc       60
atccaccagt ggcctgctac actggtgcag cctgttggaa gccctctgag cctggaatgt      120
accgtggaag gcaccagcaa tcccaacctg tactggtaca gcaggccgc tggaagagga       180 ctgcagctgc tgttttacag cgtcggcatc ggccagatca gcagcgaggt tccacagaat      240
ctgagcgcca gcagaccca ggacagacag tttatcctga gcagcaagaa gctgctgctg       300
agcgacagcg gcttctacct gtgtgcttgg agtggcagcg gcggcaatca gcctcagcac      360
tttggagatg gcacccggct gagcatcctg aagatctcc ggaacgtgac ccccctaaa       420 gtgaccctgt tcgaacccag caaggccgag atcgccaaca gcagaaagc caccctcgtg      480 tgcctggcca gaggcttctt ccccgaccat gtggaactgt cttggtgggt caacggcaaa      540
gaggtgcaca gcggagtgtc caccgaccct caggcctaca agagagcaa ctacagctac      600 tgcctgagca gcagactgcg ggtgtccgcc accttctggc acaacccccg gaaccacttc      660
aggtgccagg tgcagtttca cggcctgagc gaagaggaca gtggcccga aggctccccc       720 aagcccgtga cccagaatat ctctgccgag gcctggggca gagccgactg tggaattacc     780
agcgccagct accaccaggg cgtgctgtct gccaccatcc tgtacgagat cctgctgggc     840
aaggccaccc tgtacgccgt gctggtgtct ggcctggtgc tgatggccat ggtcaagaag     900
aagaacagct ga                                                         912

<210> SEQ ID NO 26
<211> LENGTH: 395
<212> TYPE: PRT
<213> ORGANISM: Artificial Sequence
<220> FEATURE:
<223> OTHER INFORMATION: synthetic sequence

<400> SEQUENCE: 26

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30
```

-continued

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
 50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro His His His His His Tyr Phe Ser Lys Glu
            260                 265                 270

Glu Trp Glu Lys Met Lys Ala Ser Glu Lys Ile Phe Tyr Val Tyr Met
        275                 280                 285

Lys Arg Lys Tyr Glu Ala Met Thr His His His His His Asp Lys
290                 295                 300

Thr Gly Phe His Phe Cys Gly Gly Ser Leu Ile Ser Glu Asp Trp Val
305                 310                 315                 320

Val Thr Ala Ala His Cys Gly Val Arg Thr Ser His His His His
                325                 330                 335

His Ser Ser Pro Gly Val Tyr Ala Arg Val Thr Lys Leu Ile Pro Trp
            340                 345                 350

Val Gln Lys Ile Leu Ala Ala Asn His His His His His Pro Arg
        355                 360                 365

Ala Leu Ala Glu Thr Ser Tyr Val Lys Val Leu Glu Tyr Val Ile Lys
370                 375                 380

Val Ser Ala Arg Val Arg Phe Phe Phe Pro Ser
385                 390                 395

<210> SEQ ID NO 27
<211> LENGTH: 1188
<212> TYPE: DNA
<213> ORGANISM: Artificial Sequence
<220> FEATURE:
<223> OTHER INFORMATION: synthetic sequence

<400> SEQUENCE: 27

```
atgtgggtcc cggttgtctt cctcaccctg tccgtgacgt ggattggtgc tgcaccccct c    60 atcctgtctc ggattgtggg aggctgggag tgcgagaagc attcccaacc ctggcaggtg       120
cttgtggcct ctcgtggcag ggcagtctgc ggcggtgttc tggtgcaccc ccagtgggtc       180
ctcacagctg cccactgcat caggaacaaa agcgtgatct tgctgggtcg gcacagcctg       240
tttcatcctg aagacacagg ccaggtattt caggtcagcc acagcttccc acaccgctc        300 tacgatatga gcctcctgaa gaatcgattc ctcaggccag gtgatgactc cagccacgac       360
ctcatgctgc tccgcctgtc agagcctgcc gagctcacgg atgctgtgaa ggtcatggac       420
ctgcccaccc aggagccagc actggggacc acctgctacg cctcaggctg ggcagcatt        480 gaaccagagg agttcttgac cccaaagaaa cttcagtgtg tggacctcca cgttatttcc      540
aacgacgtgt gtgcgcaagt tcaccctcag aaggtgacca agttcatgct gtgtgctgga       600
cgctggacag ggggcaaaag cacctgctcg ggtgattctg ggggcccact tgtctgtaac       660
ggtgtgcttc aaggtatcac gtcatggggc agtgaaccgt gtgccctgcc cgaaaggcct       720
tccctgtaca ccaaggtggt gcattaccgg aagtggatca aggacaccat cgtggccaac       780
ccccatcacc atcaccacca ctacttctct aaggaagagt gggaaaagat gaaagcctcg       840
gagaaaatct tctatgtgta tatgaagaga agtatgagg ctatgactca tcaccatcac        900
caccacgaca aaaccggctt ccacttctgc gggggctccc tcatcagcga ggactgggtg       960
gtcaccgctg cccactgcgg ggtcaggacc tccatcacc atcaccacca ctccagccct      1020
ggcgtgtacg cccgtgtcac caagctcata ccttgggtgc agaagatcct ggctgccaac      1080
catcaccatc accaccaccc aagggccctc gctgaaacca gctatgtgaa agtccttgag     1140
tatgtgatca aggtcagtgc aagagttcgc tttttcttcc catcctga                 1188
```

<210> SEQ ID NO 28
<211> LENGTH: 10
<212> TYPE: PRT
<213> ORGANISM: Homo sapiens

<400> SEQUENCE: 28

Lys Leu Tyr Gly Leu Asp Trp Ala Glu Leu
1               5                   10

MAGEA1 SPECIFIC T CELL RECEPTORS AND THEIR USE

FIELD OF THE INVENTION

The present invention relates to an isolated T cell receptor (TCR) specific for a MAGEA1-derived peptide and to a polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

BACKGROUND OF THE INVENTION

MAGEA1, also called Melanoma-Associated Antigen 1, is a member of the MAGEA gene family coding for a number of proteins having high homology with each other. The MAGEA antigens belong to the family of cancer/testis antigens (CTA) and were the first human tumor-associated antigens identified at the molecular level (Science 1991. 254: 1643-1647/republished in J. Immunol. 2007; 178:2617-2621). The MAGEA gene family includes 12 highly homologous genes located on chromosome Xq28. Their expression is consistently detected in cancers of different histological origin, such as non-small cell lung cancer, bladder cancer, esophageal, head and neck cancer and sarcoma, as well as myeloma, certain types of breast cancer and also in germinal cells (Front Med (Lausanne). 2017; 4: 18.). MAGEA1 is a cytosolic/cytoplasmic protein and peptides derived from the MAGEA1 protein are presented in an MHC-class I background, i.e. on HLA molecules. More specifically, MAGEA1 derived epitopes are presented on HLA-A2 molecules, indicating the antigens immunogenicity and by this suitability as a target for cancer immunotherapy. A multitude of clinical trials in the field of immunotherapy have already been conducted targeting MAGEA proteins (clinicaltrials.gov). The expression of MAGEA1 in a broad range of tumor entities like melanoma and lung cancer (Lancet Oncol 2003; 4: 104-09) with high numbers of patients in combination with the described immunogenicity of the antigen, qualifies MAGEA1 as a promising target for T cell-mediated immunotherapy. The principle of cancer immunotherapy using adoptive cell transfer (ACT) enables a highly tumor specific cancer treatment utilizing a patient's own immune system. ACT uses ex vivo expanded autologous (patient-derived) T cells genetically engineered to express T cell receptors (TCR) with a specificity for a defined epitope derived from an intracellular protein like MAGEA1. Thus, there is still a need for highly efficient TCRs which target only the tumor specific/restricted antigen MAGEA1 and therefore bear an exceptional potential for cancer immunotherapy. Thus, there is a need for such specific TCRs targeting MAGEA.

OBJECTIVES AND SUMMARY OF THE INVENTION

One objective of the present invention was the provision of a T cell receptor (TCR) which is specific for MAGEA1.

In a specific embodiment the isolated TCR comprises a TCR α chain comprising a CDR1 having the amino acid sequence of SEQ ID NO: 2, a CDR2 having the amino acid sequence of SEQ ID NO: 3 and a CDR3 having the amino acid sequence of SEQ ID NO: 4, a TCR β chain comprising a CDR1 having the amino acid sequence of SEQ ID NO: 5, a CDR2 having the amino acid sequence of SEQ ID NO: 6 and a CDR3 having the amino acid sequence of SEQ ID NO: 7.

The TCR specifically recognizes the amino acid sequence SEQ ID NO: 1 or a fragment thereof. In specific embodiments, the TCR specifically recognizes the HLA-A2 and/or HLA-A26 bound form of the amino acid sequence of SEQ ID NO: 1, preferably the HLA-A2 bound form. More specifically, the TCR specifically recognizes the amino acid sequence of SEQ ID NO: 1, which is presented by a molecule encoded by a gene selected from the group consisting of HLA-A*02:01, HLA-A*02:02, HLA-A*02:04, HLA-A*02:16, HLA-A*02:17 and HLA-A*26:01, more preferably the TCR specifically recognizes the amino acid sequence of SEQ ID NO: 1, which is presented by a molecule encoded by a gene selected from the group consisting of HLA-A*02:01, HLA-A*02:04, HLA-A*02:16 and HLA-A*02:17, even more preferably the TCR specifically recognizes the amino acid sequence of SEQ ID NO: 1, which is presented by the HLA-A*02:01 encoded molecule.

The TCR of the invention is particular useful, since it shows high tumor cell recognition capacity, high tumor cell killing capacity and high functional avidity. Moreover, the TCR shows no significant secretion of Th2 cytokines IL-4, IL-5 and IL-13, which is advantageous for effective tumor regression.

Preferably the TCR does not have cross-reactivity to other MAGEA family members.

Another objective of the present invention is the provision of T cells expressing a functional TCR being specific for MAGEA1.

The TCR according to the invention is isolated and/or purified and may be soluble or membrane bound.

In some embodiments, the amino acid sequence of the TCR may comprise one or more phenotypically silent substitutions. In addition, the TCR of the invention can be labelled. Useful labels are known in the art and can be coupled to the TCR or TCR variant using routine methods, optionally via linkers of various lengths. The term "label" or "labeling group" refers to any detectable label. Additionally, or alternatively, the amino acid sequence may be modified to comprise a therapeutic agent or pharmacokinetic modifying moiety. The therapeutic agent may be selected from the group consisting of an immune effector molecule, a cytotoxic agent and a radionuclide. The immune effector molecule may for example be a cytokine. The pharmacokinetic modifying moiety may be at least one polyethylene glycol repeating unit, at least one glycol group, at least one sialyl group or a combination thereof.

The TCR, in particular a soluble form of the TCR, according to the invention can be modified by attaching additional functional moieties, e.g. for reducing immunogenicity, increasing hydrodynamic size (size in solution), solubility and/or stability (e.g. by enhanced protection to proteolytic degradation) and/or extending serum half-life. Other useful functional moieties and modifications include "suicide" or "safety switches" that can be used to shut off or turn on effector host cells carrying an inventive TCR in a patient's body or to shut off or turn on the transgenic TCR itself. TCRs with an altered glycosylation pattern are also envisaged herein.

It is also conceivable to add a drug or a therapeutic entity, such as a small molecule compound to the TCR, in particular to a soluble form of the inventive TCR.

The TCR, in particular a soluble form of the inventive TCR, can additionally be modified to introduce additional domains which aid in identification, tracking, purification and/or isolation of the respective molecule (tags).

In some embodiments, the TCR is of the single chain type, wherein the TCR α chain and the TCR β chain are linked by a linker sequence.

Another aspect of the invention refers to a polypeptide comprising a functional portion of the TCR as described herein, wherein the functional portion comprises one of the amino acid sequences of SEQ ID NOs: 4 and 7, preferably wherein the functional portion comprises the amino acid sequences of SEQ ID NOs: 2, 3, 4 and 5, 6, 7.

In specific embodiments, the functional portion comprises the TCR α variable chain and/or the TCR β variable chain.

Specific embodiments refer to a multivalent TCR complex comprising at least two TCRs as described herein. In a more specific embodiment, at least one of said TCRs is associated with a therapeutic agent.

Some embodiments refer to the inventive TCR expressed on an effector cell, especially on an immune effector cell as a functional polypeptide or functional multivalent polypeptide, wherein IFN-γ secretion is induced in the aforementioned effector cell expressing the TCR upon binding to an HLA-A2 bound form of the amino acid sequence SEQ ID NO: 2.

Another aspect of the invention refers to a nucleic acid encoding a TCR as described herein or encoding the polypeptide as described above.

A further aspect of the invention refers to a plasmid or vector comprising the nucleic acid of the present application as described above. Preferably, the vector is an expression vector or a vector suitable for the transduction or transfection of cells, especially eukaryotic cells. The vector may be for example a retroviral vector, for example a gamma-retroviral or lentiviral vector.

Another aspect of the invention refers to a cell expressing the TCR as described herein. The cell may be an isolated primary cell or non-naturally occurring.

Another aspect of the invention refers to a cell comprising the nucleic acid as described above or the plasmid or vector as described above. More specifically, the cell may comprise:

a) an expression vector which comprises at least one nucleic acid as described above, or
b) a first expression vector which comprises a nucleic acid encoding the alpha chain of the TCR as described herein, and a second expression vector which comprises a nucleic acid encoding the beta chain of a TCR as described herein.

The cell may be a peripheral blood lymphocyte (PBL) or a peripheral blood mononuclear cell (PBMC). Typically, the cell is an immune effector cell, especially a T cell. Other suitable cell types include gamma-delta T cells and NK-like T cells and NK cells, either modified or unmodified.

Another aspect refers to an antibody or antigen binding fragment thereof specifically binding to a portion of the TCR as described herein which mediates specificity for MAGEA1. In a specific embodiment, the portion of the TCR that mediates the MAGEA1 specificity comprises the CDR3 of the alpha chain of SEQ ID NO: 4 and/or the CDR3 of the beta chain of SEQ ID NO: 7. In some embodiments the portion of the TCR that mediates the MAGEA1 specificity comprises the amino acid sequences of SEQ ID NOs: 2, 3, 4 and 5, 6, 7.

Another aspect of the invention refers to a pharmaceutical composition comprising the TCR as described herein, the polypeptide as described herein, the multivalent TCR complex as described herein, the nucleic acid as described herein, the vector as described herein, the cell as described herein, or the antibody as described herein.

Typically, the pharmaceutical composition comprises at least one pharmaceutically acceptable carrier.

Another aspect of the invention refers to the TCR as described herein, the polypeptide as described herein, the multivalent TCR complex as described herein, the nucleic acid as described herein, the vector as described herein, the cell as described herein, or the antibody as described herein for use as a medicament, in particular for use in the treatment of cancer. The cancer may be a hematological cancer or a solid tumor. The cancer may be selected from the group consisting of prostate cancer, uterine cancer, thyroid cancer, testicular cancer, renal cancer, pancreatic cancer, ovarian cancer, esophageal cancer, non-small-cell lung cancer, lung adenocarcinoma, squamous cell carcinoma, non-Hodgkin's lymphoma, multiple myeloma, melanoma, hepatocellular carcinoma, head and neck cancer, gastric cancer, endometrial cancer, cervical cancer, colorectal cancer, stomach adenocarcinoma, cholangiocarcinoma, breast cancer, bladder cancer, myeloid leukemia and acute lymphoblastic leukemia, sarcoma or osteosarcoma.

FIGURE LEGENDS

FIG. 1 shows the specific recognition of MAGEA1$_{KVL}$ (SEQ ID NO. 1) peptide (KVL)-loaded T2 cells by TCR T15.8-4.3-83-expressing effectors derived from different donors (donor A or B; bars in grey or black). The TCR-mediated target recognition as measured by secretion of IFN-γ for the TCR version with a fully murine C-region (murC) is shown in the left graph, with the minimal-murinized human C-region (mmC) in the middle graph. Recognition mediated by benchmark control MAGEA1-TCR-transduced effectors is shown on the right. As a control, T2 cells loaded with irrelevant ASTN-1 peptide (SEQ ID NO. 28) were incubated with T cells expressing the inventive TCR or control TCR (Ctrl. MAGEA1-TCR).

Figure 2:
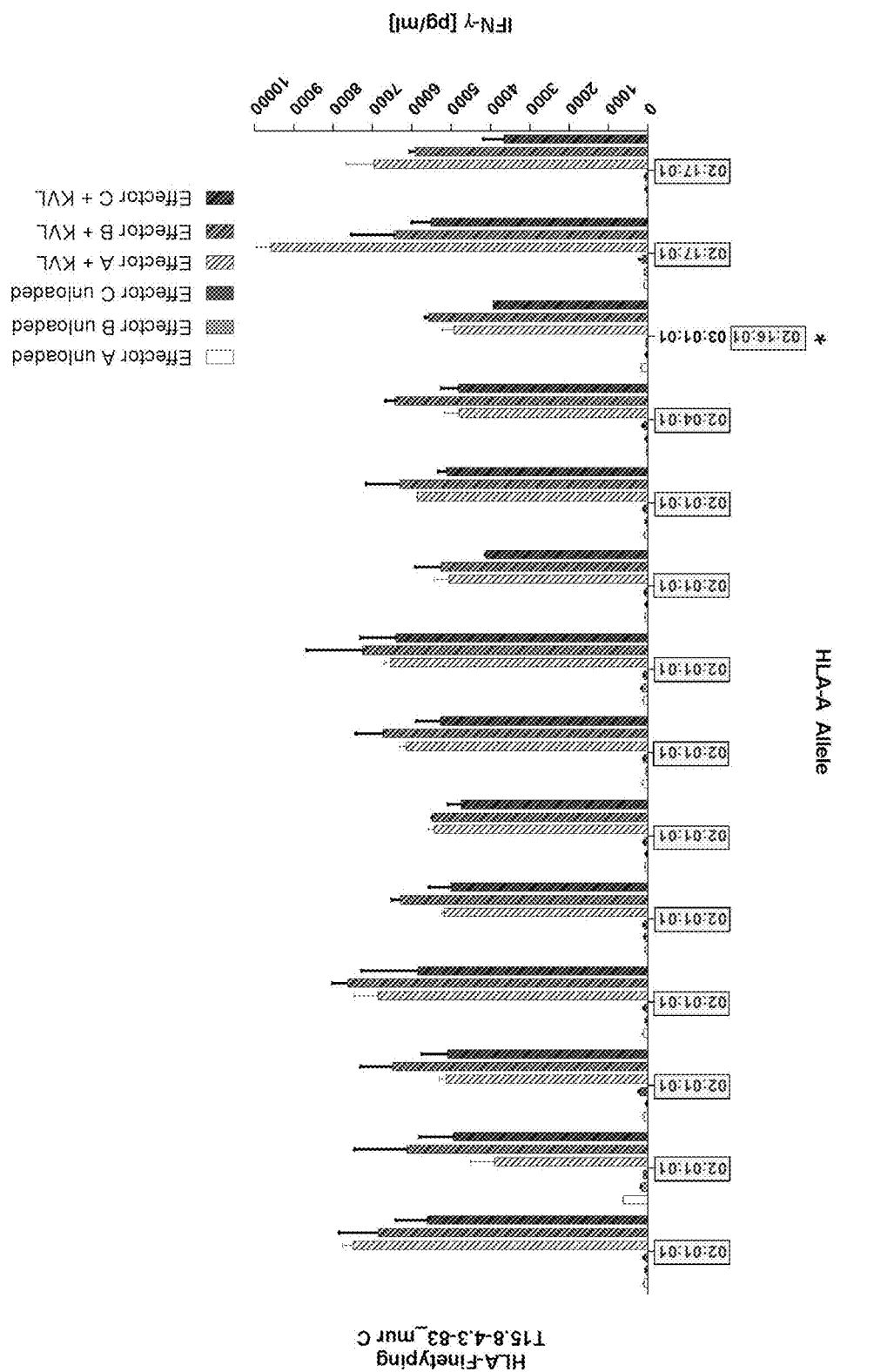

FIG. 2 shows IFN-γ secretion upon specific recognition of KVL-peptide-loaded lymphoblastoide cell lines (LCL) by TCR T15.8-4.3-83 expressed in three different effector cell preparations (shaded white, light grey and dark grey bars). No recognition is observed when unloaded LCLs were co-cultured with the respective effector cells (plain bars, white, light grey, dark grey). The boxes indicate the HLA alleles responsible for presentation and recognition. In case of LCLs heterozygous for HLA-A (as indicated by asterisk), recognition of the peptide on the other HLA-A can be excluded (data not shown).

Figure 3:
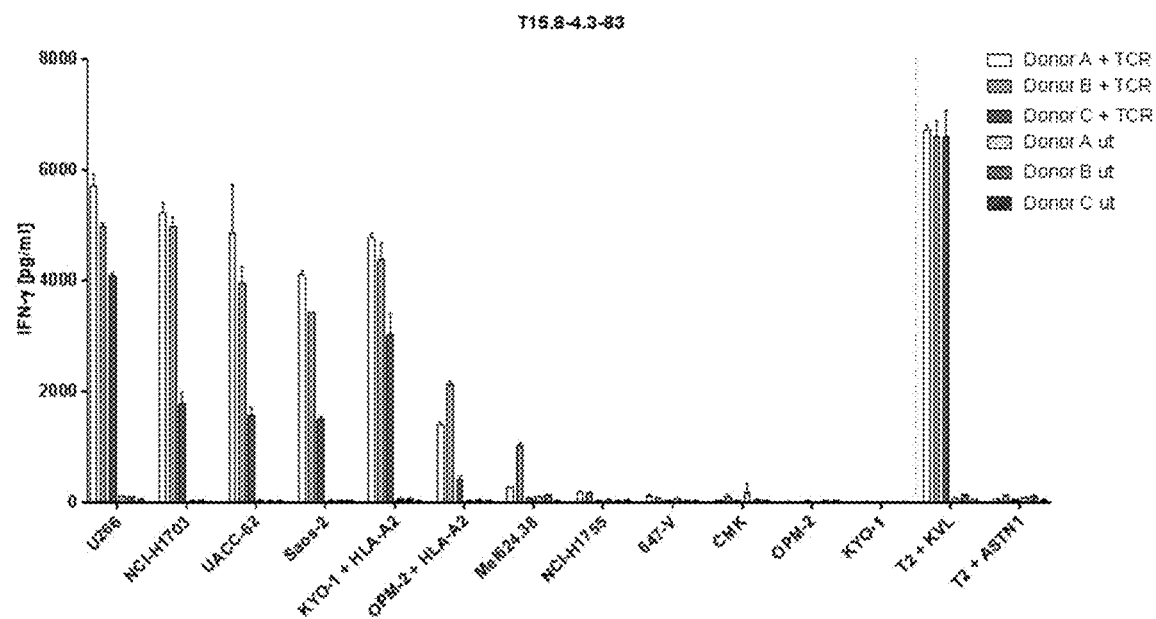
Figure 3:
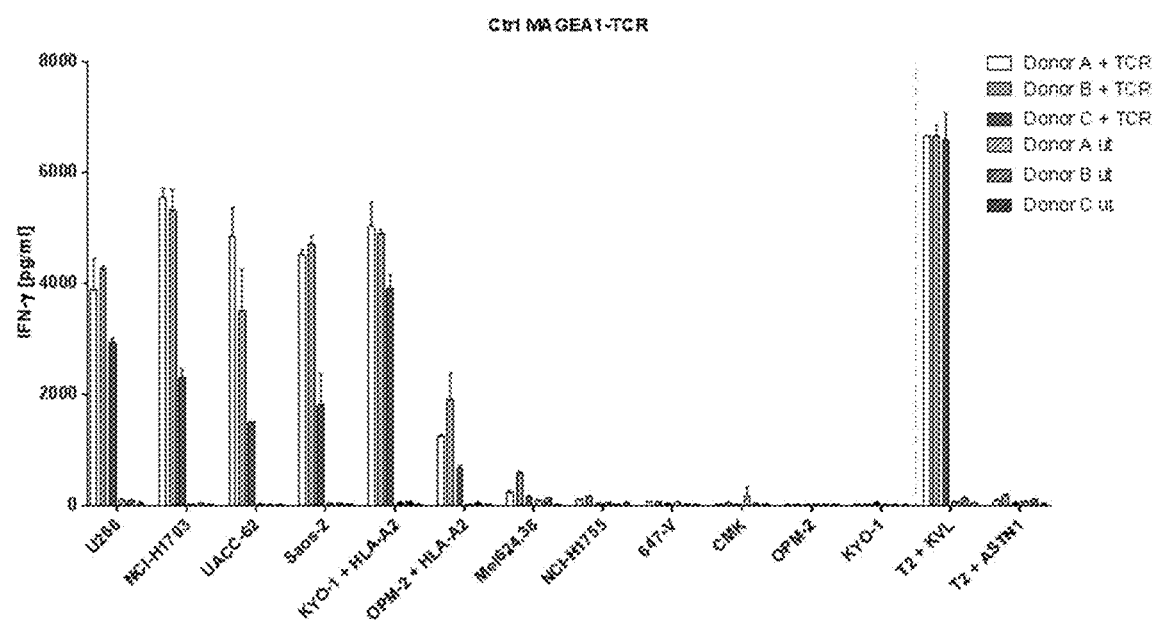
Figure 4A:
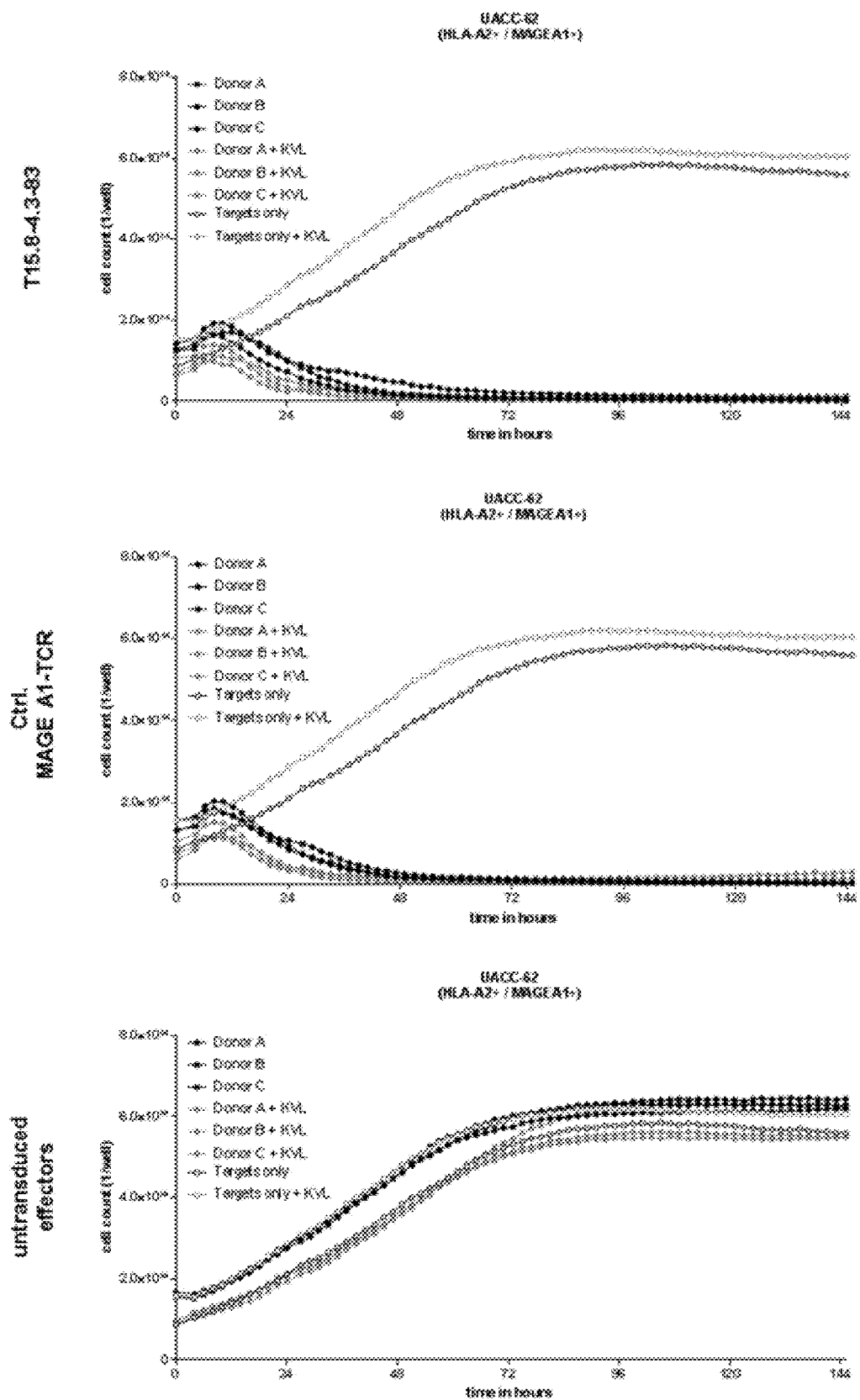
Figure 4B:
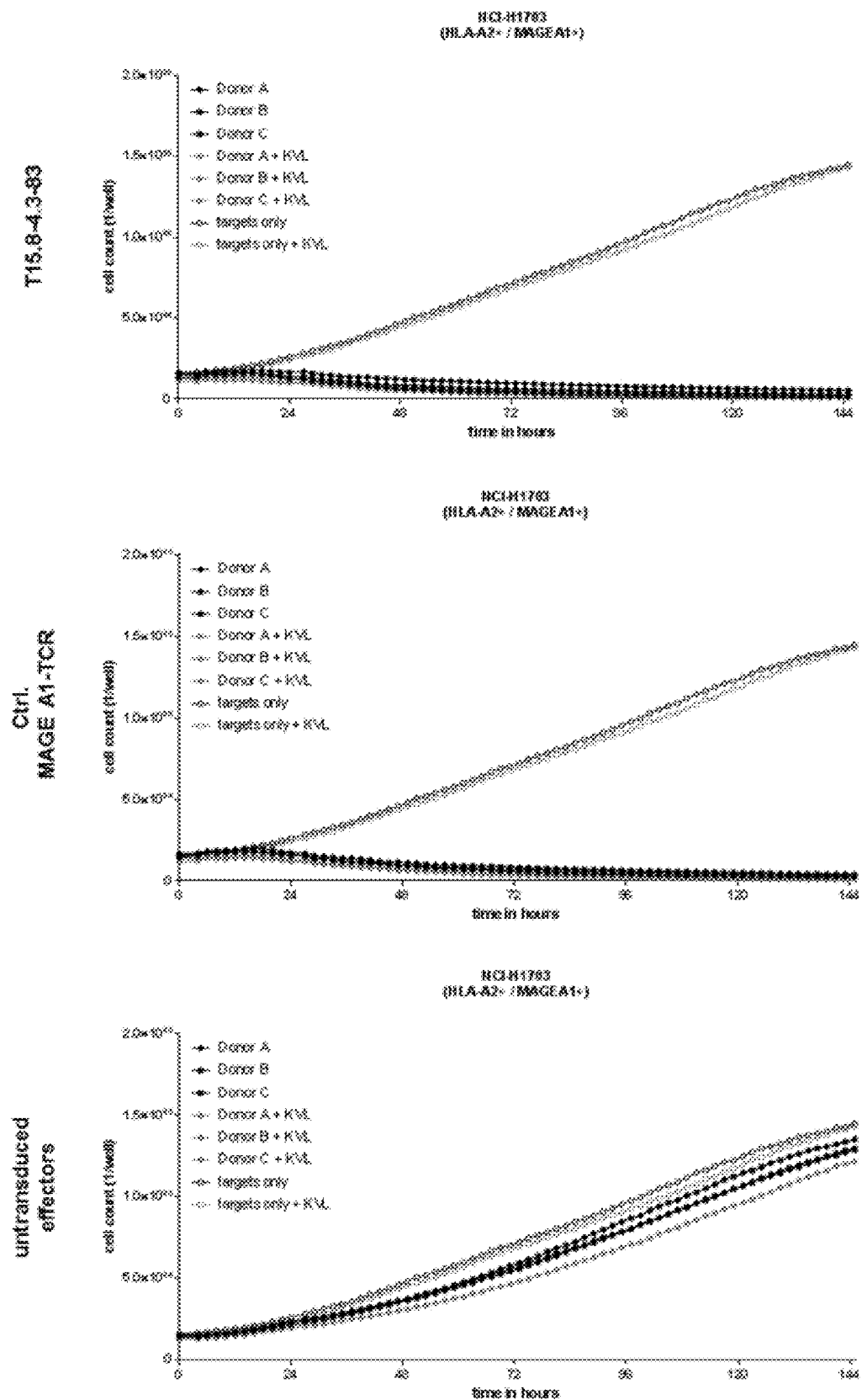
Figure 4C:
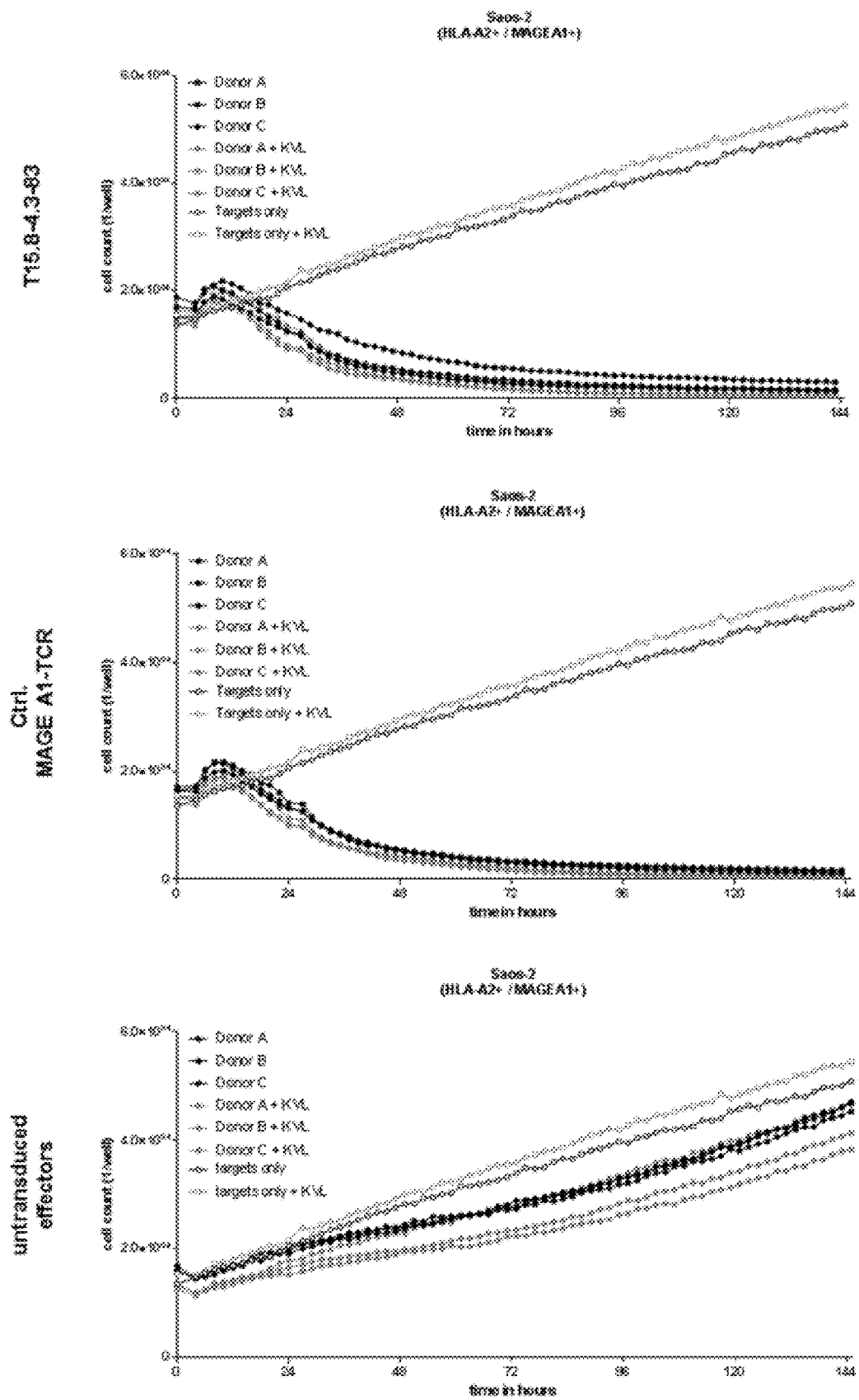
Figure 4D:
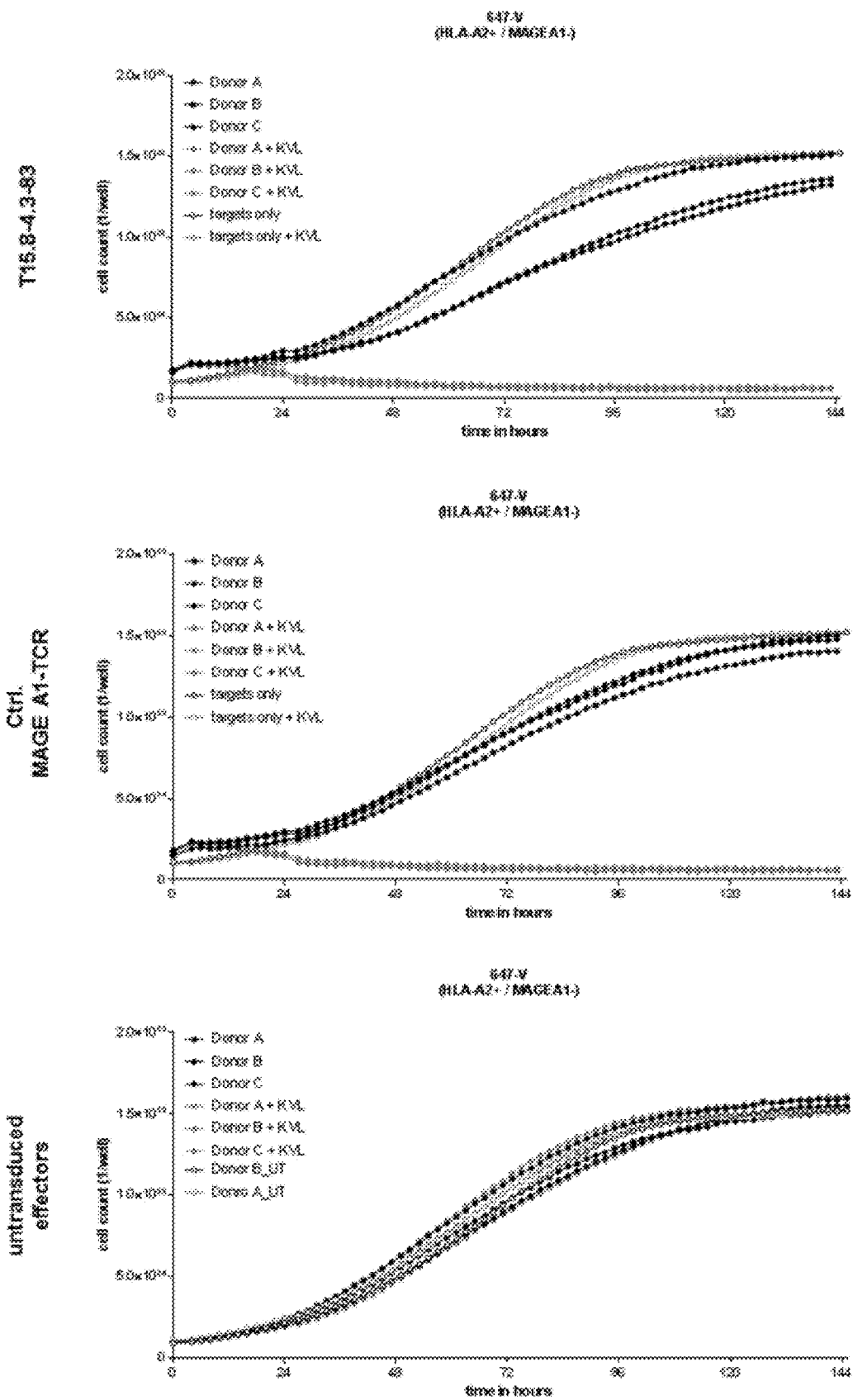

FIG. 3 depicts the recognition of various tumor cell lines of different origin mediated by TCR T15.8-4.3-83-expressing effectors (upper graph) or benchmark Ctrl. MAGEA1-TCR (lower graph). Effector cells were derived from three different donors (donor A, B or C; bars in white, light grey or dark grey). Target recognition by MAGEA1-TCR-expressing effector cells (plain bars) or untransduced control cells (shaded bars) was detected by measuring IFN-γ secretion. T2 cells loaded with the KVL peptide or loaded with the irrelevant ASTN1 peptide served as target control and are shown on the right side of each graph (T2+KVL, T2+ASTN1).

FIG. 4A to D shows the TCR-mediated lysis of the tumor cell lines UACC-62 (A), NCI-H1703 (B), Saos-2 (C) and 647-V (D). Lysis of cells was measured by the disappearance of fluorescently labelled target cells. Tumor cells were tested either unmodified (black) or loaded with the KVL peptide (grey) as positive control. The targets were co-cultured for up to 144 hours with effector cells derived from three different donors (donors A, B or C, filled circles) either expressing TCR T15.8-4.3-83 (upper graphs), benchmark Ctrl. MAGEA1-TCR (middle graph) or untransduced (lower graph). Target cells cultured alone are shown in each graph as reference (empty circles). Images were taken and analyzed every 2 h with the IncuCyte™ Zoom System, depicted are target cell counts/well over 144 h.

Figure 5:
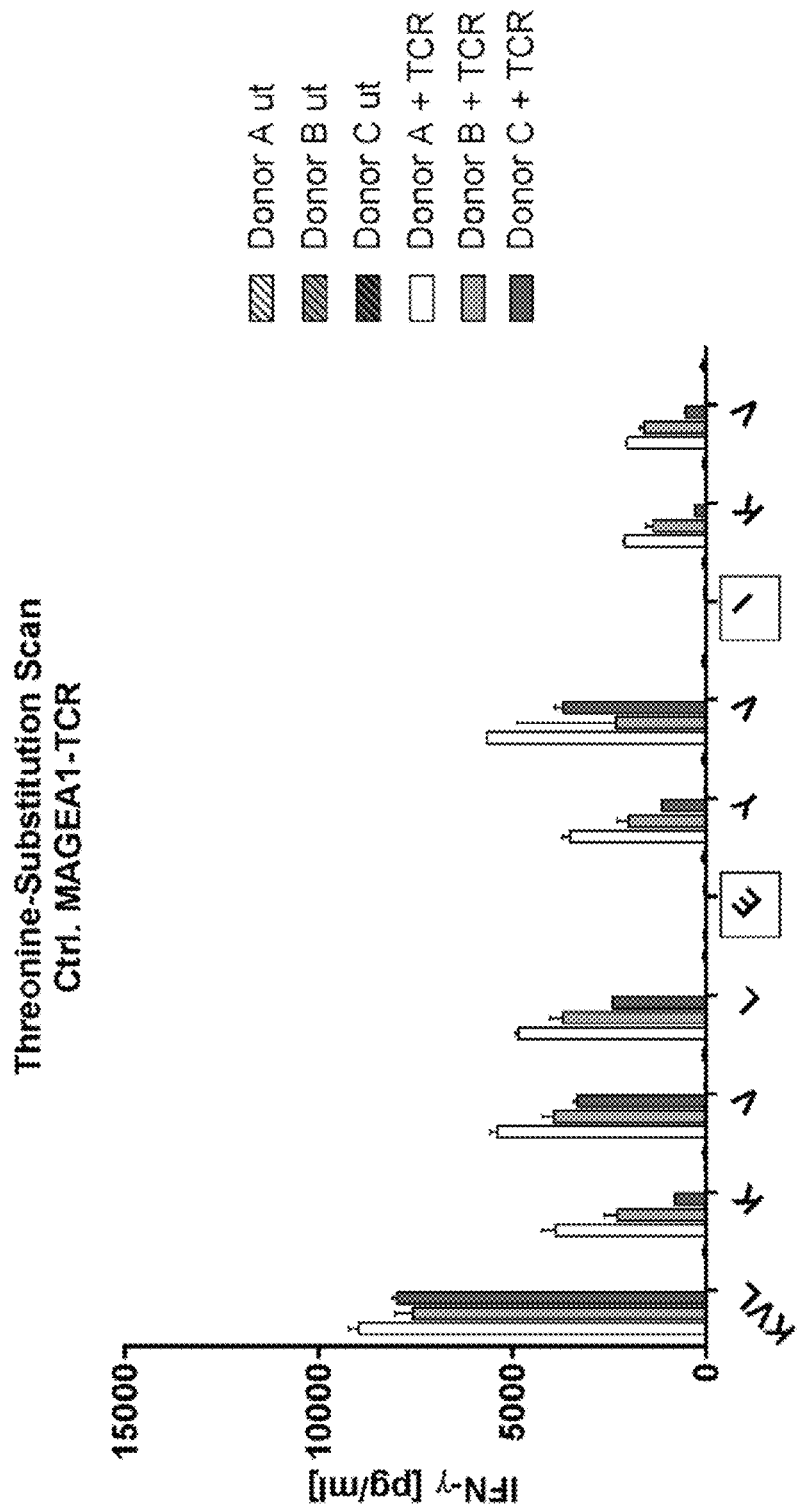

FIG. 5 shows recognition of T2 cells loaded with the peptides for the threonine-substitution scan after co-culture with benchmark ctrl. MAGEA1-TCR-transduced (plain bars) or untransduced (shaded bars) effectors from three different donors (donor A, B or C; bars in white, light grey or dark grey). Recognition of the TCR's original MAGEA1-derived epitope KVL is shown on the left. The epitope sequence shown on the x-axis indicates the position for an exchange of the original AA for threonine. An eliminated recognition by the exchange of the original AA is highlighted with black frames. Target recognition was detected by measuring T cell-mediated IFN-γ secretion.

Figure 6:
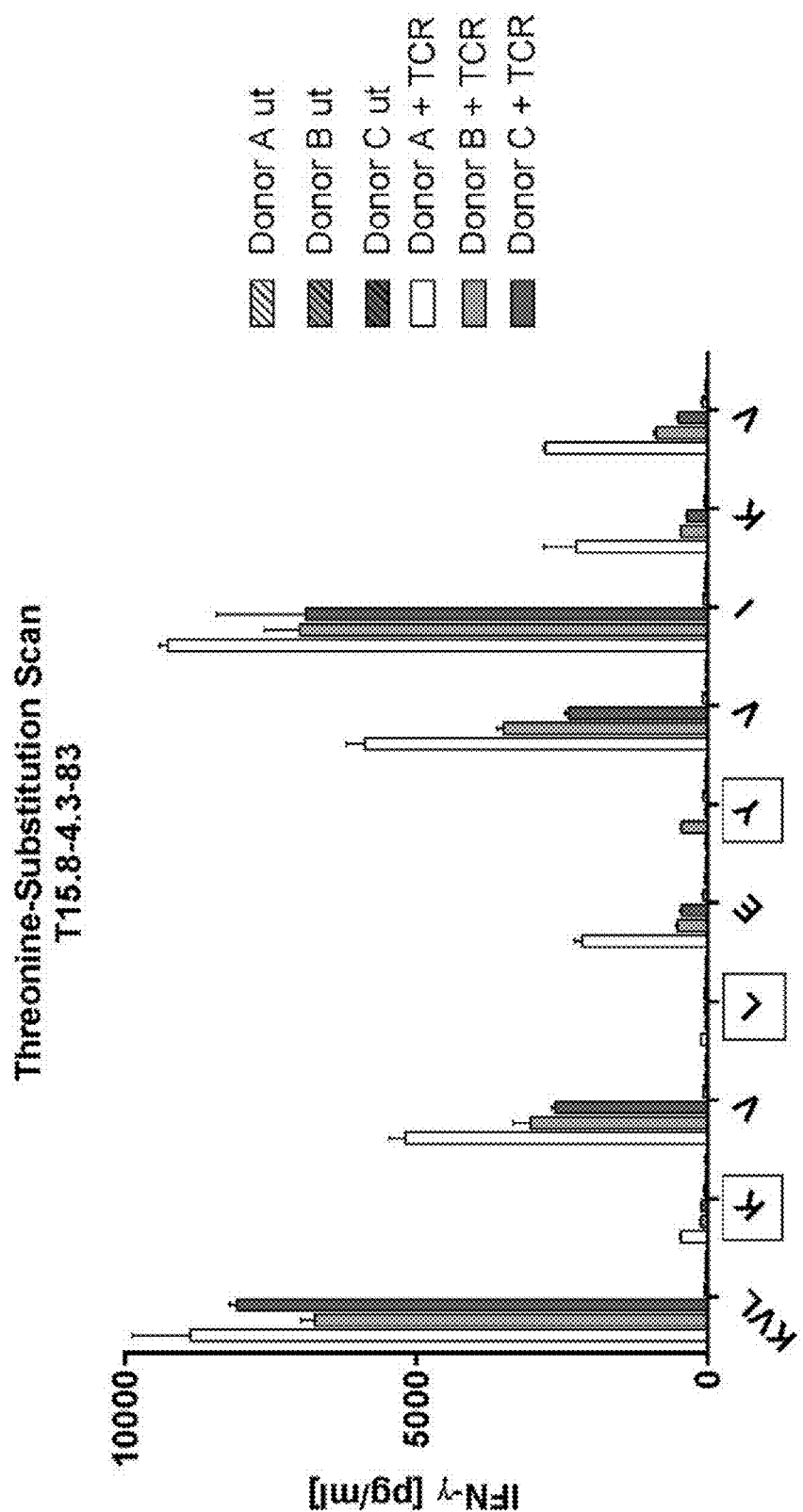

FIG. 6 shows the recognition of T2 cells loaded with the peptides for threonine-substitution scan after co-culture with TCR T15.8-4.3-83-transduced (plain bars) or untransduced (shaded bars) effectors from three different donors (donor A, B or C; bars in white, light grey or dark grey). Recognition of the TCR's original MAGEA1-derived epitope KVL is shown on the left. The epitope sequence shown on the x-axis indicates the position for an exchange of the original AA for threonine. An eliminated recognition by the exchange of the original AA is highlighted with black frames. Target recognition was detected by measuring T cell-mediated IFN-γ secretion.

Figure 7A:
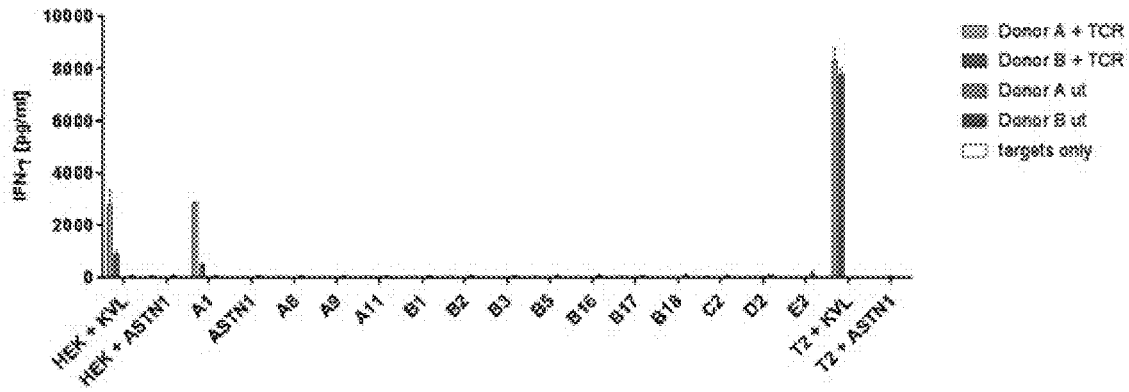
Figure 7B:
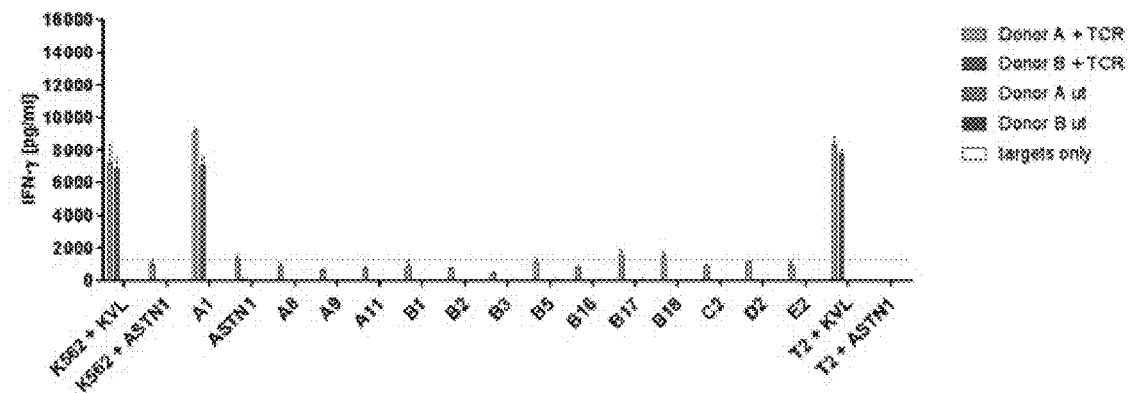
Figure 7C:
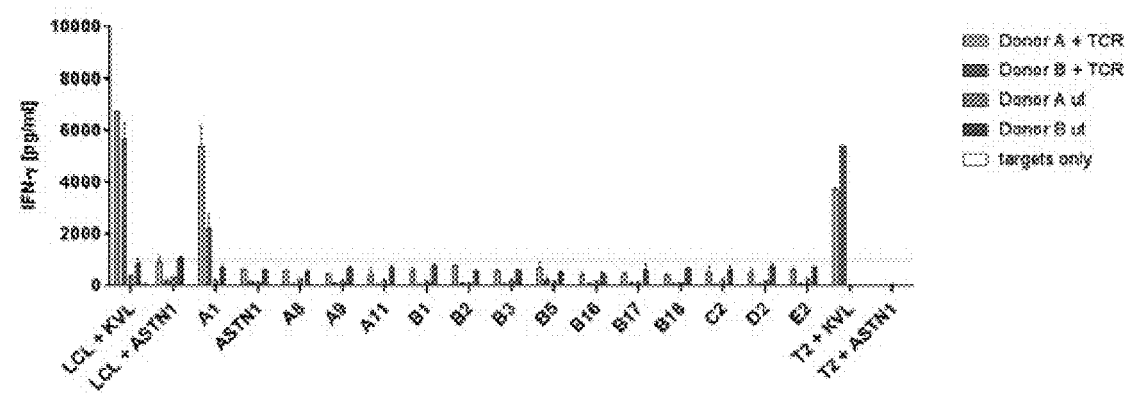

FIG. 7 shows the TCR T15.8-4.3-83-mediated recognition of HEK 293T cells (A), K562 cells (B) and LCL cells (C). The recognition of target cells was detected by measuring T cell-mediated IFN-γ secretion. The cell lines and T2 cells were either loaded with the MAGEA1-derived KVL peptide (+KVL) or the ASTN1-derived KLY peptide (+ASTN1) as controls or transfected with ivtRNA encoding MAGEA1, ASTN1 or 13 MAGE family members, as indicated on the x-axes. The targets were either co-cultured with TCR-transduced (plain bars) or untransduced (shaded bars) effector cells derived from two donors (light grey or dark grey). The background mediated by target cells cultured alone (targets only) is given in white bars. Dotted lines indicate a target independent background secretion of IFN-γ.

Figure 8:
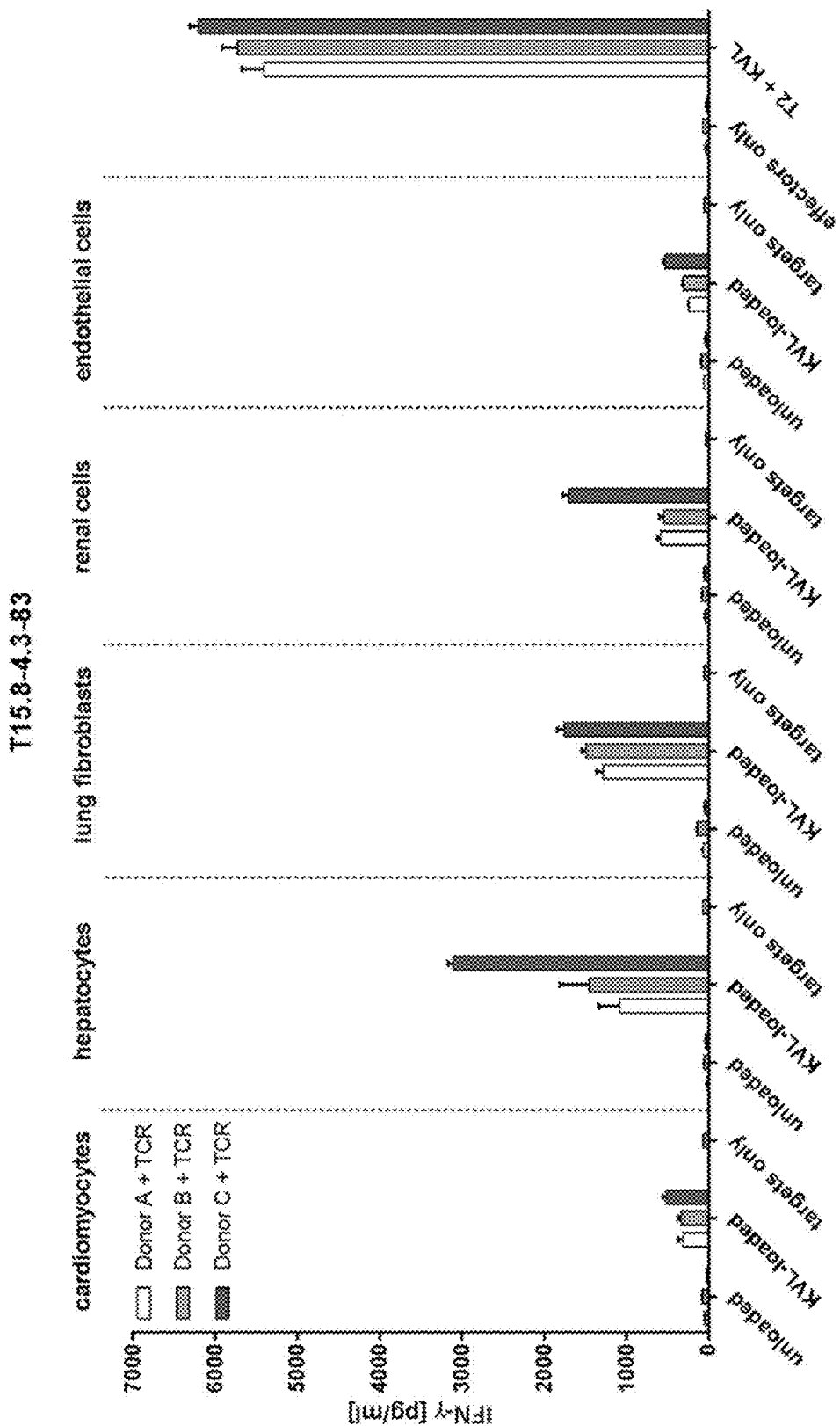

FIG. 8 shows the TCR T15.8-4.3-83-mediated recognition of unmodified (unloaded) or KVL-loaded target cells derived from healthy tissues or from induced pluripotent stem cells (iPS) representing healthy human tissues. The recognition of target cells was detected by measuring IFN-γ secretion by T cells derived from three different donors transduced with TCR T15.8-4.3-83 (donor A, B or C; bars in white, light grey or dark grey). The background IFN-γ secretion of targets alone (targets only) is shown for every cell type as a control, the recognition of T2 cells loaded with the epitope KVL (T2+KVL), recognized by the TCR and background by effectors alone (effectors only) are shown on the right side of the graph.

Figure 9:
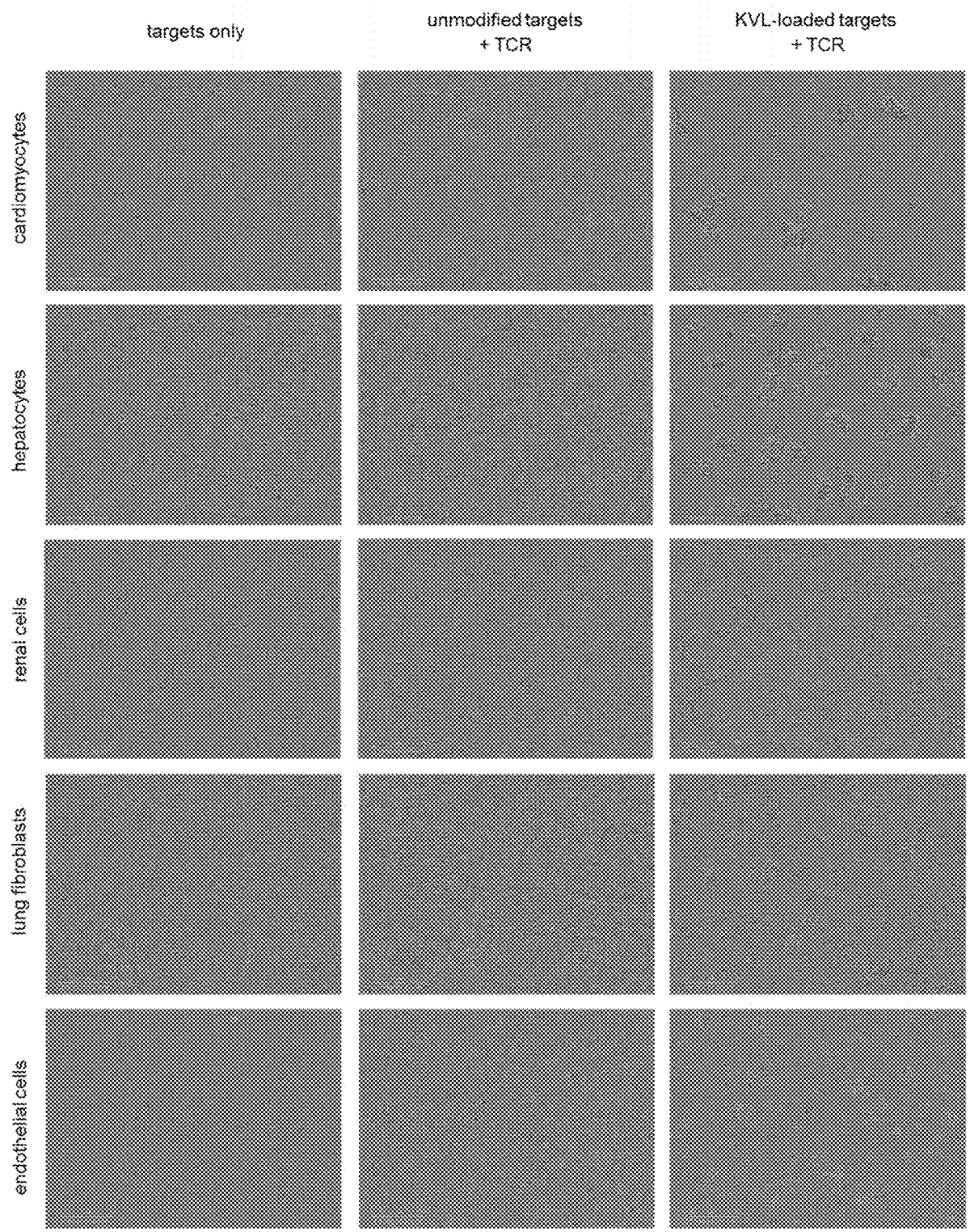

FIG. 9 shows representative pictures taken with a phase-contrast microscope of co-cultures of normal cells with effector cells. While there is a clear TCR-mediated lysis of all KVL-loaded target cells (complete disruption of the cell layer), the TCR-expressing effector cells do not lyse unmodified normal cells.

Figure 10:
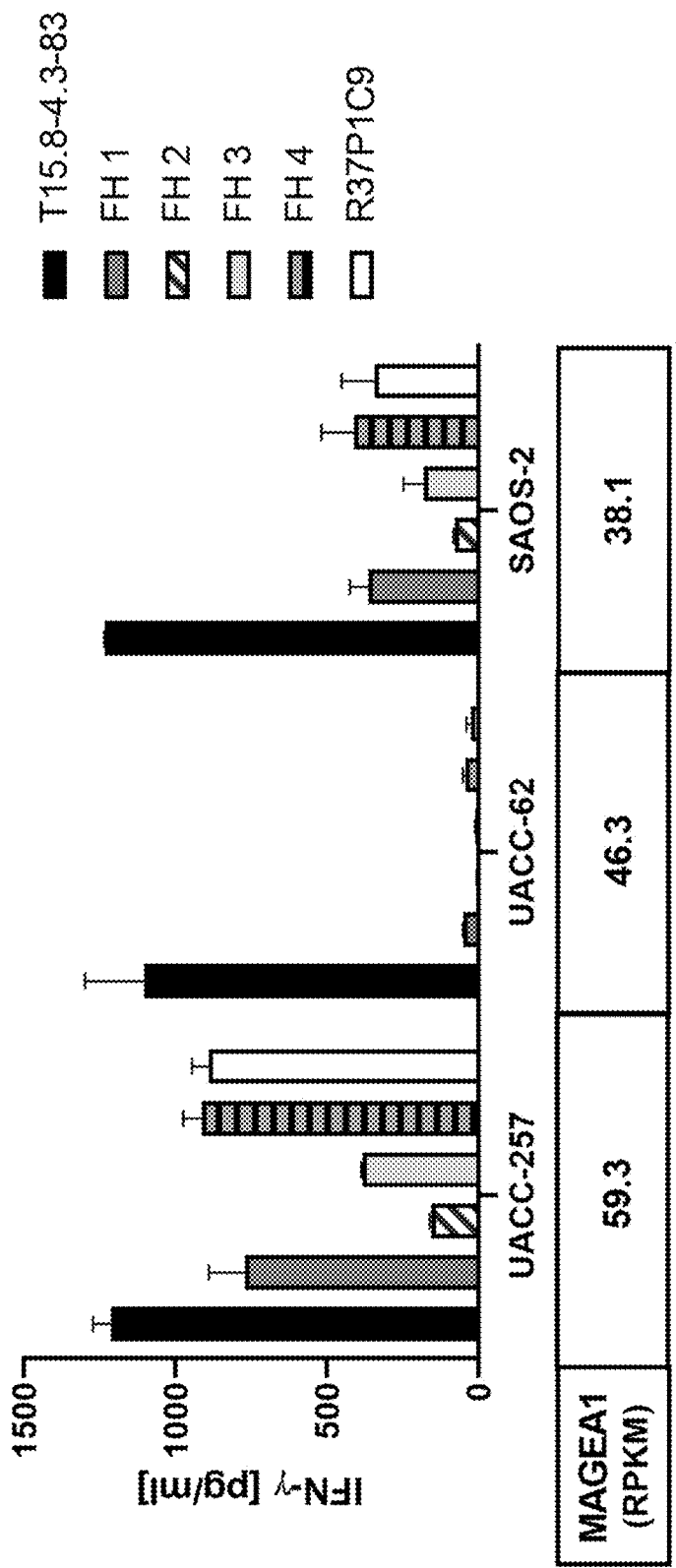

FIG. 10 shows the capacity of TCR-transgenic effector T cell populations to produce IFN-γ in response to MAGEA1 and HLA-A*02:01 double-positive tumor cell lines. FH1, FH2 FH3 and FH4 refer to the TCRs disclosed in WO 2018/170338 FH1: Vα=SEQ ID NO.:7 of WO'338 Vβ=SEQ ID NO: 5 of WO'338; FH2: Vα=SEQ ID NO.: 11 Vβ=SEQ ID NO.: 9 of WO'338, FH3: Vα=SEQ ID NO.:15 of WO'338 Vβ=SEQ ID NO: 13 of WO'338; FH1: Vα=SEQ ID NO.:19 of WO'338 Vβ=SEQ ID NO: 17 of WO'338; R37P1C9 refers to the MAGA1-TCR disclosed in WO2018/104438.

Figure 11:
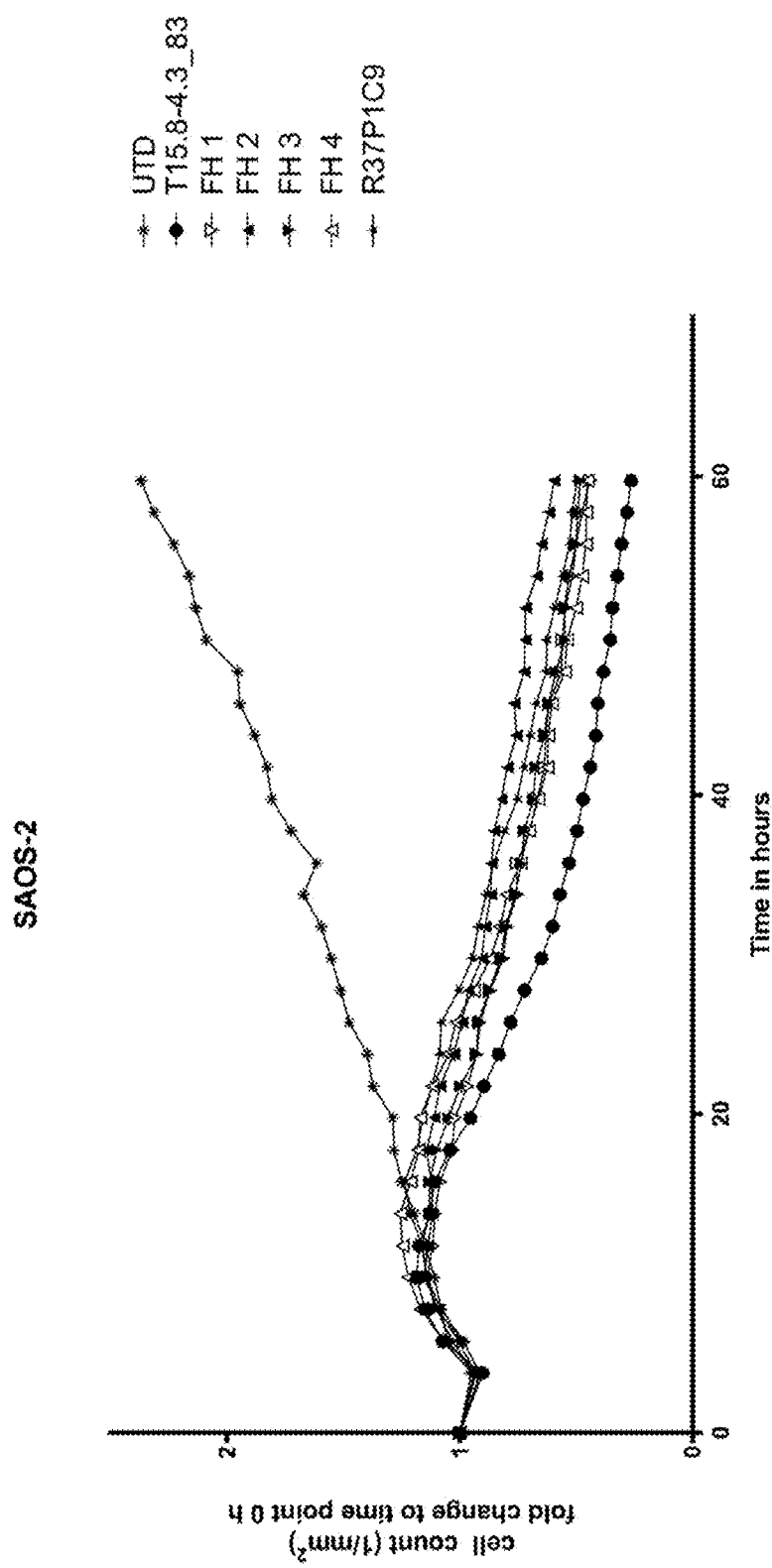

FIG. 11 shows the capacity of TCR-transgenic effector T cell populations to lyse MAGEA1 and HLA-A*02:01 double-positive tumor cell lines. FH1, FH2 FH3 and FH4 refer to the TCRs disclosed in WO 2018/170338 (see FIG. 10). R37P1C9 refers to the MAGA1-TCR disclosed in WO2018/104438. UTD: untransduced.

Figure 12:
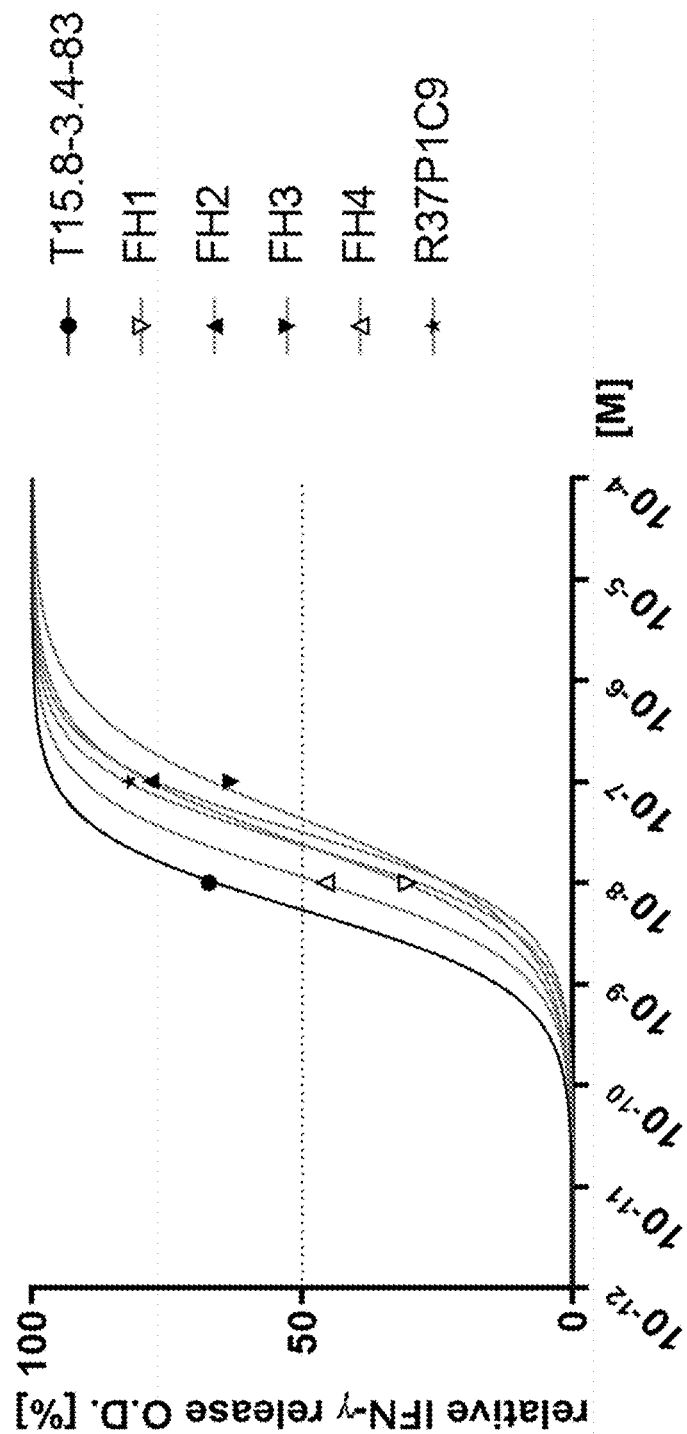

FIG. 12 shows the functional avidity of different KVL peptide-specific TCRs. Functional avidity refers to the accumulated strength of multiple affinities of individual non-covalent binding interactions between the transgenic TCR and the pMHC complex. FH1, FH2 FH3 and FH4 refer to the TCRs disclosed in WO 2018/170338 (see FIG. 10). R37P1C9 refers to the MAGA1-TCR disclosed in WO2018/104438.

Figure 13:
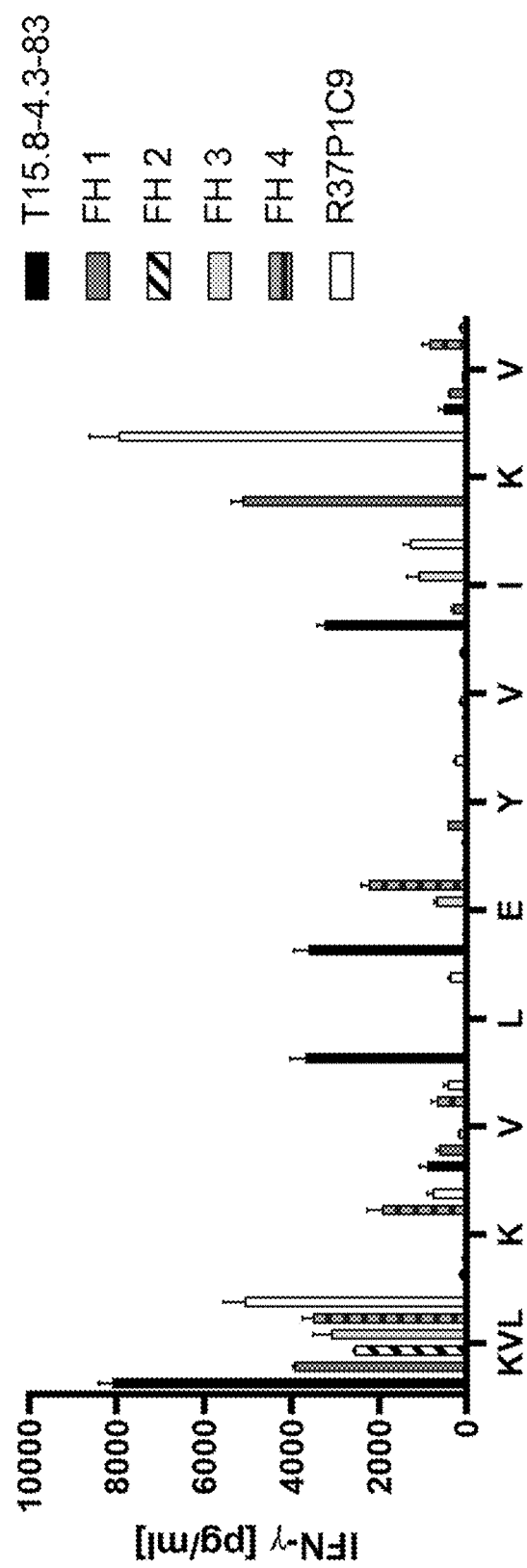

FIG. 13 Serine residues are used to systematically replace individual amino acids in the MAGEA1$_{KVL}$ peptide (Serine Scan) in order to determine critical amino acids in the epitope sequence.

Figure 14A:
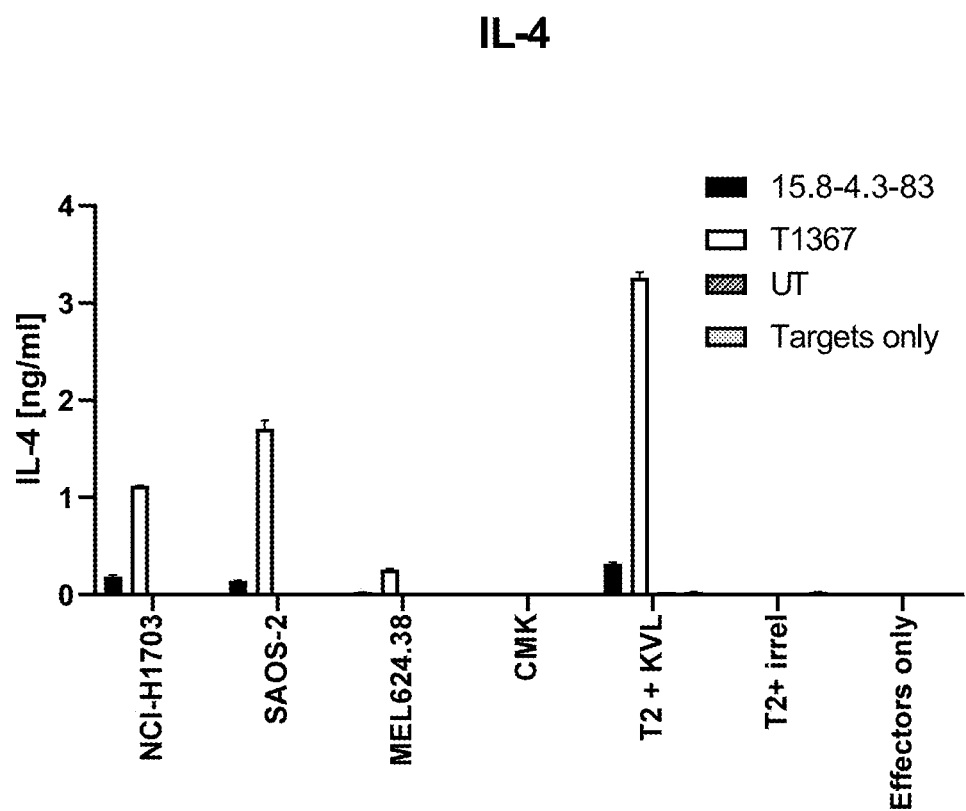
Figure 14B:
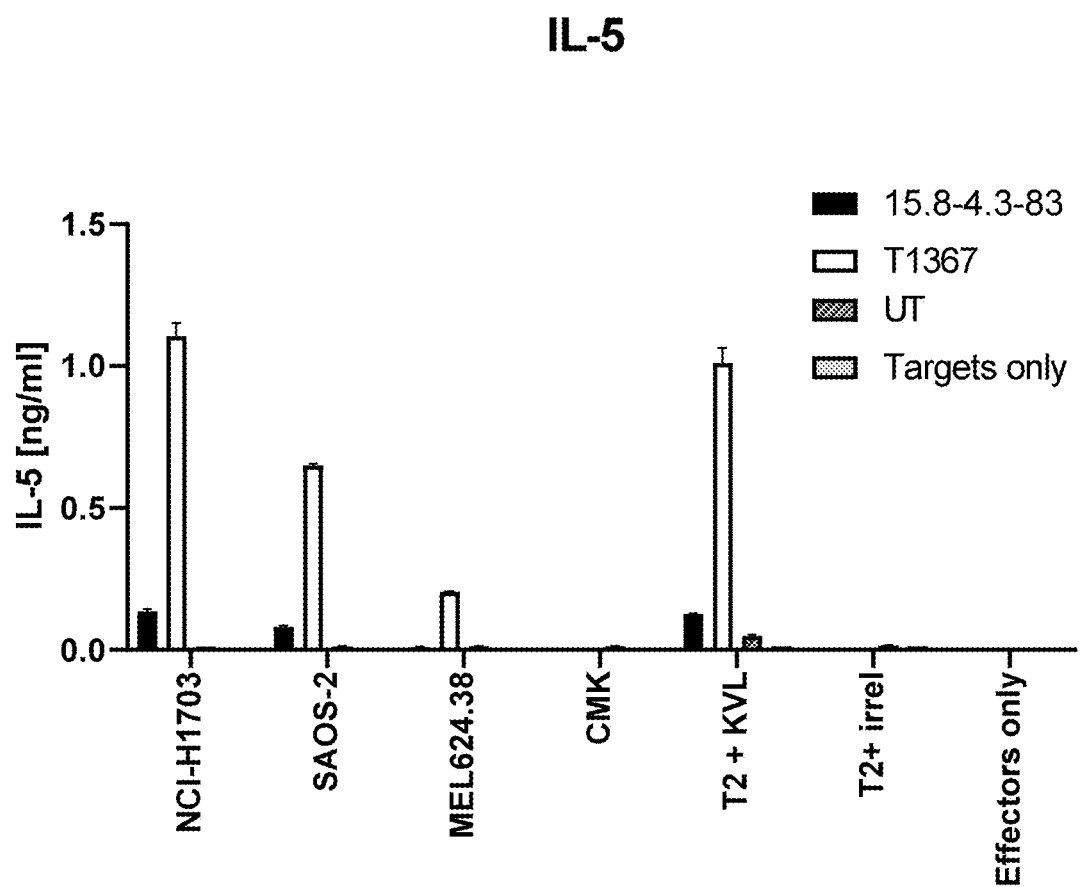
Figure 14C:
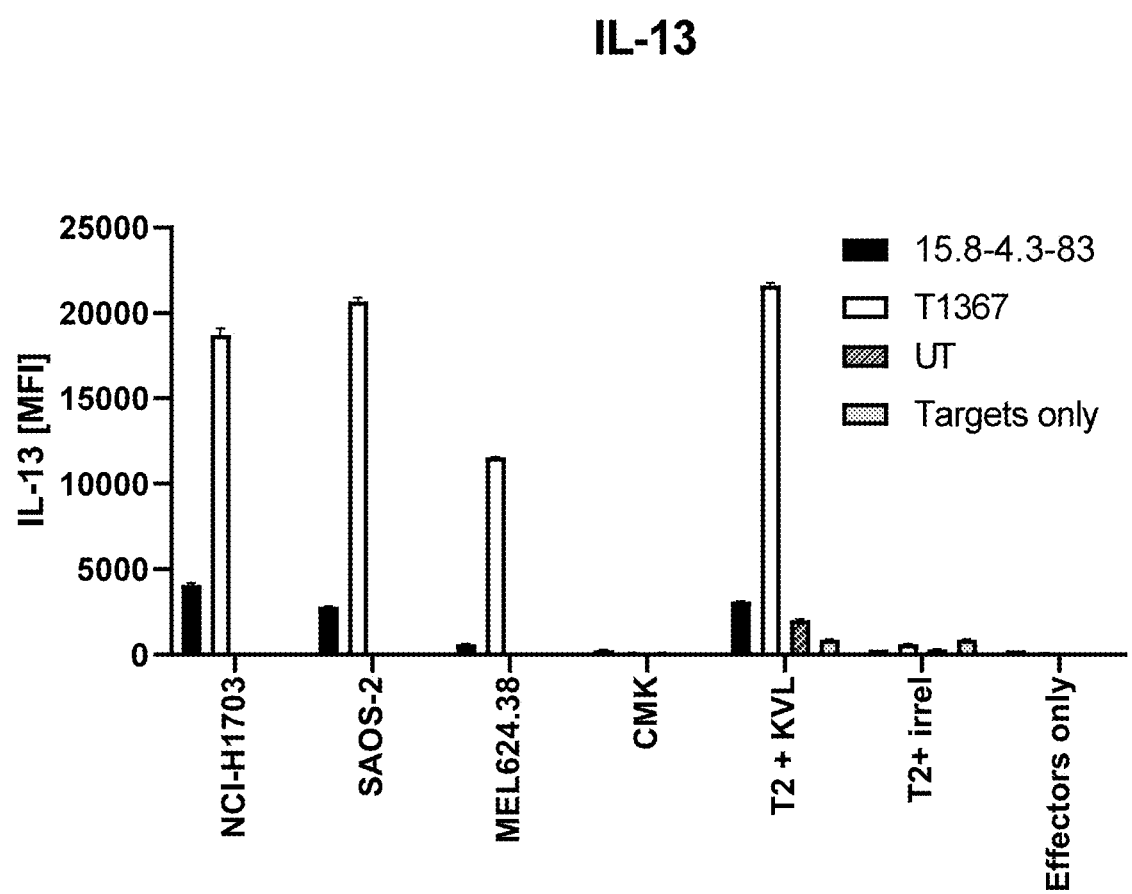

FIG. 14 shows the secretion pattern of the TH2 specific cytokines IL-4, IL-5 and IL-13 of T cells transduced with different TCRs. UT: untransfected. T1367 denotes the TCR disclosed in WO2014/118236. Targets only: tumor cells are cultured without TCR.

DETAILED DESCRIPTION OF THE INVENTION

Before the invention is described in detail with respect to some of its preferred embodiments, the following general definitions are provided.

The present invention as illustratively described in the following may be suitably practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense or meaning to the person skilled in the art. If a specific meaning is conveyed to certain terms, definitions of terms will be given in the following in the context of which the terms are used.

TCR Background

A TCR is composed of two different and separate protein chains, namely the TCR alpha (α) and the TCR beta (β) chain. The TCR α chain comprises variable (V), joining (J) and constant (C) regions. The TCR β chain comprises variable (V), diversity (D), joining (J) and constant (C) regions. The rearranged V(D)J regions of both the TCR α and the TCR β chain contain hypervariable regions (CDR, complementarity determining regions), among which the CDR3 region determines the specific epitope recognition. At the C-terminal region both TCR α chain and TCR β chain contain a hydrophobic transmembrane domain and end in a short cytoplasmic tail.

Typically, the TCR is a heterodimer of one α chain and one β chain. This heterodimer can bind to MHC molecules presenting a peptide.

The term "variable TCR α region" or "TCR α variable chain" or "variable domain" in the context of the invention refers to the variable region of a TCR α chain. The term "variable TCR β region" or "TCR β variable chain" in the context of the invention refers to the variable region of a TCR β chain.

The TCR loci and genes are named using the International Immunogenetics (IMGT) TCR nomenclature (IMGT Database, www.IMGT.org; Giudicelli, V., et al. IMGT/LIGM-DB, the IMGT® comprehensive database of immunoglobulin and T cell receptor nucleotide sequences, Nucl. Acids Res., 34, D781-D784 (2006). PMID: 16381979; T cell Receptor Factsbook, LeFranc and LeFranc, Academic Press ISBN 0-12-441352-8).

Target

The target for the herein described TCR is MAGEA1 (NCBI Reference Sequence: NM_004988.4)-derived peptide KVL (SEQ ID NO: 1)

TCR Specific Sequence

Some embodiments relate to an isolated TCR comprising a TCR α chain and a TCR β chain, wherein
the TCR α chain comprises a complementarity-determining region 3 (CDR3) having the sequence of SEQ ID NO: 4,
the TCR β chain comprises a CDR3 having the amino acid sequence of SEQ ID NO: 7.

Specific embodiments refer to an isolated TCR comprising:
a TCR α chain comprising a CDR1 having the amino acid sequence of SEQ ID NO: 2, a CDR 2 having the amino acid sequence of SEQ ID NO: 3 and a CDR 3 having the sequence of SEQ ID NO: 4.
a TCR β chain comprising a CDR1 having the amino acid sequence of SEQ ID NO: 5, a CDR 2 having the amino acid sequence of SEQ ID NO: 6 and a CDR 3 having the sequence of SEQ ID NO: 7.

In some embodiments, the TCR comprises a variable TCR α region having an amino acid sequence which is at least 80%, at least 85%, at least 90%, at least 95%, at least 96%, at least 97%, at least 98%, at least 99% identical to SEQ ID NO: 8 and a variable TCR β region having an amino acid sequence which is at least 80%, at least 85%, at least 90%, at least 95%, at least 96%, at least 97%, at least 98%, at least 99% identical to SEQ ID NO: 9.

A preferred embodiment relates to a TCR comprising a variable TCR α region having the amino acid sequence of SEQ ID NO: 8 and a variable TCR β region having the amino acid sequence of SEQ ID NO: 9.

The TCR originating from T cell clone T15.8-4.3-83 which, in its transgenic form is used in the examples, comprises a TCR α chain comprising a complementarity-determining region 3 (CDR3) having the sequence of SEQ ID NO: 4 and a TCR β chain comprising a CDR3 having the amino acid sequence of SEQ ID NO: 7. In particular, the inventive TCR comprises a variable TCR α region having the amino acid sequence of SEQ ID NO: 8 and a variable TCR β region having the amino acid sequence of SEQ ID NO: 9.

As can be seen from the examples the TCRs according to the invention are specific for MAGEA1 and exhibit only very low cross-reactivity to other epitopes or antigens.

Other embodiments relate to an isolated TCR comprising a TCR α chain having an amino acid sequence which is at least 80%, at least 85%, at least 90%, at least 95%, at least 96%, at least 97%, at least 98%, at least 99% identical to SEQ ID NO: 10 and a TCR β chain having an amino acid sequence which is at least 80%, at least 85%, at least 90%, at least 95%, at least 96%, at least 97%, at least 98%, at least 99% identical to SEQ ID NO: 11.

Specific embodiments refer to a TCR comprising a TCR α chain having the amino acid sequence of SEQ ID NO: 10 and a TCR β chain having the amino acid sequence of SEQ ID NO: 11. Thus, the TCR described herein that is specific for the complex of HLA-A*02:01 with the MAGEA1 peptide of SEQ ID NO: 1 comprises a Vα chain encoded by the TRAV19*01 gene and a Vβ gene encoded by the TRAV30*01 gene.

Other embodiments refer to an isolated TCR comprising a TCR α chain and a TCR β chain, wherein
the variable TCR α region has an amino acid sequence which is at least 80%, at least 85%, at least 90%, at least 95%, at least 96%, at least 97%, at least 98%, at least 99% identical to SEQ ID NO: 8 and comprises a CDR3 region set out in SEQ ID NO: 3;
the variable TCR β region has an amino acid sequence which is at least 80%, at least 85%, at least 90%, at least 95%, at least 96%, at least 97%, at least 98%, at least 99% identical to SEQ ID NO: 9 and comprises a CDR3 region set out in SEQ ID NO: 7.

The determination of percent identity between multiple sequences is preferably accomplished using the AlignX application of the Vector NTI Advance™ 10 program (Invitrogen Corporation, Carlsbad CA, USA). This program uses a modified Clustal W algorithm (Thompson et al., 1994. Nucl Acids Res. 22: pp. 4673-4680; Invitrogen Corporation; Vector NTI Advance™ 10 DNA and protein sequence analysis software. User's Manual, 2004, pp. 389-662). The determination of percent identity is performed with the standard parameters of the AlignX application.

The TCR according to the invention is isolated or purified. "Isolated" in the context of the invention means that the TCR is not present in the context in which it originally occurred in nature. "Purified" in the context of the invention means e.g. that the TCR is free or substantially free of other proteins and non-protein parts of the cell it originates from.

In some embodiments, the amino acid sequence of the TCR may comprise one or more phenotypically silent substitutions.

"Phenotypically silent substitutions" are also named "conservative amino acid substitutions". The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides. The ordinarily skilled artisan can readily and routinely screen variant amino acids and/or the nucleic acids encoding them to determine if these variations substantially reduce or destroy the ligand binding capacity by methods known in the art.

The skilled person understands that also the nucleic acid encoding the TCR may be modified. Useful modifications in the overall nucleic acid sequence include codon optimization of the sequence. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

According to some embodiments of the invention the amino acid sequence of the TCR is modified to comprise a detectable label, a therapeutic agent or pharmacokinetic modifying moiety.

Non-limiting examples for detectable labels are radiolabels, fluorescent labels, nucleic acid probes, enzymes and contrast reagents. Therapeutic agents which may be associated with the TCRs include radioactive compounds, immune-modulators, enzymes or chemotherapeutic agents. The therapeutic agents could be enclosed by a liposome linked to TCR so that the compound can be released slowly at the target site. This will avoid damaging during the transport in the body and ensure that the therapeutic agent, e.g. toxin, has maximum effect after binding of the TCR to the relevant antigen presenting cells. Other examples for therapeutic agents are:
 peptide cytotoxins, i.e. proteins or peptides with the ability to kill mammalian cells, such as ricin, diphtheria toxin, pseudomonas bacterial exotoxin A, DNase and RNase. Small molecule cytotoxic agents, i.e. compounds with the ability to kill mammalian cells having a molecular weight of less than 700 Daltons. Such compounds could contain toxic metals capable of having a cytotoxic effect. Furthermore, it is to be understood that these small molecule cytotoxic agents also include pro-drugs, i.e. compounds that decay or are converted under physiological conditions to release cytotoxic agents. Such agents may for example include docetaxel, gemcitabine, cisplatin, maytansine derivatives, rachelmycin, calicheamicin, etoposide, ifosfamide, irinotecan, porfimer sodium photofrin II, temozolomide, topotecan, trimetrexate glucoronate, mitoxantrone, auristatin E, vincristine and doxorubicin; radionuclides, such as, iodine 131, rhenium 186, indium 111, yttrium 90. bismuth 210 and 213, actinium 225 and astatine 213. The association of the radionuclides with the TCRs or derivatives thereof may for example be carried out by chelating agents; immune-stimulators, also known as immunostimulants, i.e. immune effector molecules which stimulate immune response. Exemplary immune-stimulators are cytokines such as IL-2 and IFN-γ, antibodies or fragments thereof, including anti-T cell or NK cell determinant antibodies (e.g anti-CD3, anti-CD28 or anti-CD16); alternative protein scaffolds with antibody like binding characteristics; Superantigens, i.e. antigens that cause non-specific activation of T-cells resulting in polyclonal T cell activation and massive cytokine release, and mutants thereof; chemokines such as IL-8, platelet factor 4, melanoma growth stimulatory protein, etc. complement activators; xenogeneic protein domains, allogeneic protein domains, viral/bacterial protein domains, viral/bacterial peptides.

The antigen receptor molecules (T cell receptor molecules) on human T lymphocytes are non-covalently associated with the CD3 (T3) molecular complex on the cell surface. Perturbation of this complex with anti-CD3 monoclonal antibodies induces T cell activation. Thus, some embodiments refer to a TCR as described herein associated (usually by fusion to an N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab')2 fragments, dsFv and scFv fragments, Nanobodies™ (Ablynx (Belgium), molecules comprising synthetic single immunoglobulin variable heavy chain domain derived from a camelid (e.g. camel or llama) antibody) and Domain Antibodies (comprising an affinity matured single immunoglobulin variable heavy chain domain or immunoglobulin variable light chain domain (Domantis (Belgium)) or alternative protein scaffolds that exhibit antibody-like binding characteristics such as Affibodies (comprising engineered protein A scaffold Affibody (Sweden)) or Anticalins (comprising engineered anticalins Pieris (German)).

The therapeutic agent may preferably be selected from the group consisting of an immune effector molecule, a cytotoxic agent and a radionuclide. Preferably, the immune effector molecule is a cytokine.

The pharmacokinetic modifying moiety may be for example at least one polyethylene glycol repeating unit, at least one glycol group, at least one sialyl group or a combination thereof. The association of at least one polyethylene glycol repeating unit, at least one glycol group, at least one sialyl group may be caused in a number of ways known to those skilled in the art. In a preferred embodiment the units are covalently linked to the TCR. The TCRs according to the invention can be modified by one or several pharmacokinetic modifying moieties. In particular, the soluble form of the TCR is modified by one or several pharmacokinetic modifying moieties. The pharmacokinetic modifying moiety may achieve beneficial changes to the pharamacokinetic profile of the therapeutic, for example improved plasma half-life, reduced or enhanced immunogenicity, and improved solubility.

The TCR according to the invention may be soluble or membrane bound. The term "soluble" refers to a TCR being in soluble form (i.e. having no transmembrane or cytoplasmic domains), for example for use as a targeting agent for delivering therapeutic agents to the antigen presenting cell. For stability, soluble αβ heterodimeric TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full-length chains having both cytoplasmic and transmembrane domains. TCRs may contain a disulfide bond corresponding to that found in nature between the respective alpha and beta constant domains, additionally or alternatively a non-native disulfide bond may be present.

The TCR, in particular a soluble form of the TCR according to the invention can thus be modified by attaching additional functional moieties, e.g. for reducing immunogenicity, increasing hydrodynamic size (size in solution) solubility and/or stability (e.g. by enhanced protection to proteolytic degradation) and/or extending serum half-life.

Other useful functional moieties and modifications include "suicide" or "safety switches" that can be used to shut off effector host cells carrying an inventive TCR in a patient's body. An example is the inducible Caspase 9 (iCasp9) "safety switch" described by Gargett and Brown Front Pharmacol. 2014; 5: 235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" "safety switches" are known in the art, e.g. Herpes Simplex Virus thymidine kinase (HSV-TK), expression of CD20 and subsequent depletion using anti-CD20 antibody or myc tags (Kieback et al, Proc Natl Acad Sci USA. 2008 Jan. 15; 105(2):623-8).

TCRs with an altered glycosylation pattern are also envisaged herein. As is known in the art, glycosylation patterns can depend on the amino acid sequence (e.g., the presence or absence of particular glycosylation amino acid residues, discussed below) and/or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. Similarly, deglycosylation (i.e., removal of carbohydrate moieties present on the binding molecule) may be accomplished chemically, e.g. by exposing the TCRs to trifluoromethanesulfonic acid, or enzymatically by employing endo- and exo-glycosidases.

It is also conceivable to add a drug such as a small molecule compound to the TCR, in particular a soluble form of the inventive TCR. Linkage can be achieved via covalent bonds, or non-covalent interactions such as through electrostatic forces. Various linkers, known in the art, can be employed in order to form the drug conjugates.

The TCR, in particular a soluble form of the inventive TCR can additionally be modified to introduce additional domains which aid in identification, tracking, purification and/or isolation of the respective molecule (tags). Thus, in some embodiments, the TCR α chain or the TCR β chain may be modified to comprise an epitope tag.

Epitope tags are useful examples of tags that can be incorporated into the TCR of the invention. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques.

Tags can further be employed for stimulation and expansion of host cells carrying an inventive TCR by cultivating the cells in the presence of binding molecules (antibodies) specific for said tag.

In general, the TCR can be modified in some instances with various mutations that modify the affinity and the off-rate of the TCR with the target antigen. In particular, the mutations may increase the affinity and/or reduce the off-rate. Thus, the TCR may be mutated in at least one CDR and the variable domain framework region thereof.

However, in a preferred embodiment the CDR regions of the TCR are not modified or in vitro affinity maturated such as for the TCR receptors in the examples. This means that the CDR regions have naturally occurring sequences. This can be advantageous, since in vitro affinity maturation may lead to immunogenicity to the TCR molecule. This may lead to the production of anti-drug antibodies decreasing or inactivating the therapeutic effect and the treatment and/or induce adverse effects.

The mutation may be one or more substitution(s), deletion(s) or insertions(s). These mutations may be introduced by any suitable method known in the art, such as polymerase chain reaction, restriction enzyme-based cloning, ligation independent cloning procedures, which are described for Example in Sambrook, Molecular Cloning— $4^{th}$ Edition (2012) Cold Spring Harbor Laboratory Press.

Theoretically, unpredictable TCR specificity with the risk for cross-reactivity can occur due to mispairing between endogenous and exogenous TCR chains. To avoid mispairing of TCR sequences, the recombinant TCR sequence may be modified to contain minimal murinized Cα and Cβ regions, a technology that has been shown to efficiently enhance correct pairing of several different transduced TCR chains. Murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells genetically modified ex vivo to express the TCRs of desired antigenic specificity, but still retaining and expressing their "original" TCRs. Nine amino acids responsible for the improved expression of murinized TCRs have been identified (Sommermeyer and Uckert, J Immunol. 2010 Jun. 1; 184(11):6223-31) and it is envisaged to substitute one or all of the amino acid residues in the TCRs alpha and/or beta chain constant region for their murine counterpart residues. This technique is also referred to as "minimal murinization" and offers the advantage of enhancing cell surface expression while, at the same time, reducing the number of "foreign" amino acid residues in the amino acid sequence and, thereby, the risk of immunogenicity.

Some embodiments refer to an isolated TCR as described herein, wherein the TCR is of the single chain type, wherein the TCR α chain and the TCR β chain are linked by a linker sequence.

A suitable single chain TCR form comprises a first segment constituted by an amino acid sequence corresponding to a variable TCR α region, a second segment constituted by an amino acid sequence corresponding to a variable TCR β region fused to the N terminus of an amino acid sequence corresponding to a TCR β chain constant region extracellular sequence, and a linker sequence linking the C terminus of the first segment to the N terminus of the second segment. Alternatively, the first segment may be constituted by an amino acid sequence corresponding to a TCR β chain variable region, the second segment may be constituted by an amino acid sequence corresponding to a TCR α chain variable region sequence fused to the N terminus of an amino acid sequence corresponding to a TCR α chain constant region extracellular sequence. The above single chain TCRs may further comprise a disulfide bond between the first and second chains, and wherein the length of the linker sequence and the position of the disulfide bond being such that the variable domain sequences of the first and second segments are mutually orientated substantially as in native T cell receptors. More specifically the first segment may be constituted by an amino acid sequence corresponding to a TCR α chain variable region sequence fused to the N terminus of an amino acid sequence corresponding to a TCR α chain constant region extracellular sequence, the second segment may be constituted by an amino acid sequence corresponding to a TCR β chain variable region fused to the N terminus of an amino acid sequence corresponding to TCR β chain constant region extracellular sequence, and a disulfide bond may be provided between the first and second chains. The linker sequence may be any sequence which does not impair the function of the TCR.

In the context of the present invention, a "functional" TCR α and/or β chain fusion protein shall mean a TCR or TCR variant, for example modified by addition, deletion or substitution of amino acids, that maintains at least substantial biological activity. In the case of the α and/or β chain of a TCR, this shall mean that both chains remain able to form a T-cell receptor (either with a non-modified α and/or β chain or with another inventive fusion protein α and/or β chain) which exerts its biological function, in particular binding to the specific peptide-MHC complex of said TCR, and/or functional signal transduction upon specific peptide:MHC interaction.

In specific embodiments the TCR may be modified, to be a functional T-cell receptor (TCR) α and/or β chain fusion protein, wherein said epitope-tag has a length of between 6 to 15 amino acids, preferably 9 to 11 amino acids. In another embodiment the TCR may be modified to be a functional T-cell receptor (TCR) α and/or β chain fusion protein wherein said T-cell receptor (TCR) α and/or β chain fusion protein comprises two or more epitope-tags, either spaced apart or directly in tandem. Embodiments of the fusion protein can contain 2, 3, 4, 5 or even more epitope-tags, as long as the fusion protein maintains its biological activity/ activities ("functional").

Preferred is a functional T-cell receptor (TCR) α and/or β chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. myc, T7, GST, GFP tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

TCR Variants

Another aspect of the invention refers to a polypeptide comprising a functional portion of the TCR of as described herein, wherein the functional portion comprises at least one of the amino acid sequences of SEQ ID NOs: 4 and 7.

The functional portion may mediate the binding of the TCR to the antigen, in particular to the antigen-MHC complex.

In one embodiment, the functional portion comprises the TCR α variable chain and/or the TCR β variable chain as described herein.

The TCR variant molecule may have the binding properties of the TCR receptor but may be combined with signaling domains of effectors cells (other than T cells), in particular with signaling domains of NK cells. Therefore, some embodiments refer to a protein comprising a functional portion of the TCR as described herein in combination with the signaling domains of an effector cell, such as a NK cell.

Another aspect of the invention refers to a multivalent TCR complex comprising at least two TCRs as described herein. In one embodiment of this aspect, at least two TCR molecules are linked via linker moieties to form multivalent complexes. Preferably, the complexes are water soluble, so the linker moiety should be selected accordingly. It is preferable that the linker moiety is capable of attaching to defined positions on the TCR molecules, so that the structural diversity of the complexes formed is minimized. One embodiment of the present aspect is provided by a TCR complex of the invention wherein the polymer chain or peptidic linker sequence extends between amino acid residues of each TCR which are not located in a variable region sequence of the TCR. Since the complexes of the invention may be for use in medicine, the linker moieties should be chosen with due regard to their pharmaceutical suitability, for example their immunogenicity. Examples of linker moieties which fulfil the above desirable criteria are known in the art, for example the art of linking antibody fragments.

Examples for linkers are hydrophilic polymers and peptide linkers. Examples for hydrophilic polymers are polyalkylene glycols. The most commonly used of this class are based on polyethylene glycol or PEG. However, others are based on other suitable, optionally substituted, polyalkylene glycols which include polypropylene glycol, and copolymers of ethylene glycol and propylene glycol. Peptide linkers are comprised of chains of amino acids, and function to produce simple linkers or multimerization domains onto which TCR molecules can be attached.

One embodiment refers to a multivalent TCR complex, wherein at least one of said TCRs is associated with a therapeutic agent.

Cytokine and Chemokine Release

Some embodiments refer to the isolated TCR as described herein, polypeptide as described herein, multivalent TCR complex as described herein, wherein IFN-γ secretion is induced by binding of the inventive TCR expressed on an effector cell to the HLA-A*02 bound form of the amino acid sequence selected from the group consisting of SEQ ID NO: 1.

The IFN-γ secretion induced by binding of the inventive TCR expressed on an effector cell to the HLA-A*02 bound form of the amino acid sequence selected from the group consisting of SEQ ID NO:1 may be more than 500 pg/ml, such as more than 1000 pg/ml, more than 2000 pg/ml, more preferably more than 4000 pg/ml, most preferably even more than 6000 pg/ml. The IFN-γ secretion may be at least 5 times higher when binding to the HLA-A*02 bound form of the amino acid sequence of SEQ ID NO: 1 compared to binding to the HLA-A*02 bound form of an irrelevant peptide (e.g. SEQ ID No: 28).

The "effector cell" may be a peripheral blood lymphocyte (PBL) or a peripheral blood mononuclear cell (PBMC). Typically, the effector cell is an immune effector cell, especially a T cell. Other suitable cell types include gamma-delta T cells and NK-like T cells.

The invention relates also to methods for identifying a TCR or a fragment thereof that binds to the target amino acid sequence SEQ ID NO: 1 or the HLA-A*02, preferably or the HLA-A*02:01 bound form thereof, wherein the method comprises contacting the candidate TCR or fragment thereof with the amino acid sequences of SEQ ID NO: 1 or the HLA-A*02, preferably or the HLA-A*02:01 bound form thereof and determining whether the candidate TCR or fragment thereof binds to the target and/or mediates an immune response.

Whether the candidate TCR or fragment thereof mediates an immune response can be determined for example by the measurement of cytokine secretion, such as IFN-γ secretion. As described above cytokine secretion may be measured by an in vitro assay in which K562 cells (or other APCs) transfected with ivtRNA coding the amino acid sequence SEQ ID NO: 1 are incubated with CD8+ enriched PBMC expressing the TCR or a molecule comprising a fragment of the TCR to be investigated.

In a particular embodiment, the TCR of the invention shows no significant secretion of the Th2 cytokines IL-4, IL-5 and IL-13. This may be advantageous, since the Th2 cytokine response may increase tumor progression (Jager M J, Desjardins L, Kivelä T, Damato BE (eds): Current Concepts in Uveal Melanoma. Dev Ophthalmol. Basel, Karger, 2012, vol 49, pp 137-149, J Immunother. 2018 October; 41(8):369-378).

Nucleic Acids, Vectors

Another aspect of the invention refers to a nucleic acid encoding a TCR as described herein or encoding the polynucleotide encoding a TCR as described herein.

| Peptide sequence SEQ ID NO | nucleotide sequence SEQ ID NO | description |
|---|---|---|
| 2 | 14 | TCR α chain CDR1 |
| 3 | 15 | TCR α chain CDR2 |
| 4 | 16 | TCR α chain CDR3 |
| 5 | 17 | TCR β chain CDR1 |
| 6 | 18 | TCR β chain CDR2 |
| 7 | 19 | TCR β chain CDR3 |
| 8 | 20 | TCR α chain variable region |
| 9 | 21 | TCR β chain variable region |
| 10 | 22 | TCR α chain complete (minimal murinized constant region) |
| 11 | 23 | TCR β chain complete (minimal murinized constant region) |

-continued

| Peptide sequence SEQ ID NO | nucleotide sequence SEQ ID NO | description |
|---|---|---|
| 12 | 24 | TCR α chain complete (murine constant region) |
| 13 | 25 | TCR β chain complete (murine constant region) |

"Nucleic acid molecule" generally means a polymer of DNA or RNA, which can be single-stranded or double-stranded, synthesized or obtained (e.g., isolated and/or purified) from natural sources which can contain natural, non-natural or altered nucleotides, and which can contain a natural, non-natural or altered internucleotide linkage, such as a phosphoroamidate linkage or a phosphorothioate linkage instead of the phosphodiester found between the nucleotides of an unmodified oligonucleotide. Preferably, the nucleic acids described herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art or commercially available (e.g. from Genscript, Thermo Fisher and similar companies). See, for example, Sambrook et al. for example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). The nucleic acid can comprise any nucleotide sequence which encodes any of the recombinant TCRs, polypeptides, or proteins, or functional portions or functional variants thereof.

The present disclosure also provides variants of the isolated or purified nucleic acids wherein the variant nucleic acids comprise a nucleotide sequence that has at least 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence encoding the TCR described herein. Such variant nucleotide sequence encodes a functional TCR that specifically recognizes MAGEA1.

The disclosure also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence.

Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand and are particularly suitable for detecting expression of any of the TCRs described herein. It is generally appreciated that conditions can be rendered more stringent by the addition of increasing amounts of formamide.

As already described elsewhere herein, the nucleic acid encoding the TCR may be modified. Useful modifications in the overall nucleic acid sequence may be codon optimization. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

Another embodiment refers to a vector comprising the nucleic acid encoding the TCR as described herein.

The vector is preferably a plasmid, shuttle vector, phagemide, cosmid, expression vector, retroviral vector, adenoviral vector or particle and/or vector to be used in gene therapy.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence (e.g. a nucleic acid of the invention). The vector may comprise DNA or RNA and/or comprise liposomes. The vector may be a plasmid, shuttle vector, phagemide, cosmid, expression vector, retroviral vector, lentiviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

Preferably, the vector is an expression vector. More preferably, the vector is a retroviral vector, more specifically a gamma-retroviral or lentiviral vector.

Cells, Cell Lines

Another aspect of the invention refers to a cell expressing the TCR as described herein.

In some embodiments, the cell is isolated or non-naturally occurring.

In specific embodiments, the cell may comprise the nucleic acid encoding the TCR as described herein or the vector comprising said nucleic acid.

In the cell the above described vector comprising a nucleic acid sequence coding for the above described TCR may be introduced or ivtRNA coding for said TCR may be introduced. The cell may be a peripheral blood lymphocyte such as a T cell. The method of cloning and exogenous expression of the TCR is for example described in Engels et al. (Relapse or eradication of cancer is predicted by peptide-major histocompatibility complex affinity. Cancer Cell, 23(4), 516-26. 2013). The transduction of primary human T cells with a lentiviral vector is, for example, described in Cribbs "simplified production and concentration of lentiviral vectors to achieve high transduction in primary human T cells" BMC Biotechnol. 2013; 13: 98.

The term "transfection" and "transduction" are interchangeable and refer to the process by which an exogenous nucleic acid sequence is introduced in a host cell, e.g. in an eukaryotic host cell. It is noted that introduction or transfer of nucleic acid sequences is not limited to the mentioned methods but can be achieved by any number of means including electroporation, microinjection, gene gun delivery, lipofection, superfection and the mentioned infection by retroviruses or other suitable viruses for transduction or transfection.

Some embodiments refer to a cell comprising:
a) an expression vector which comprises at least one nucleic acid as described herein, or
b) a first expression vector which comprises a nucleic acid encoding the alpha chain of the TCR as described herein, and a second expression vector which comprises a nucleic acid encoding the beta chain of a TCR as described herein.

In some embodiments, the cell is a peripheral blood lymphocyte (PBL) or a peripheral blood mononuclear cell (PBMC). The cell may be a natural killer cell or a T cell. Preferably, the cell is a T cell. The T cell may be a CD4+ or a CD8+ T cell. In some embodiments the cell is a stem cell like memory T cell.

Stem cell-like memory T cells (TSCM) are a less-differentiated subpopulation of CD8+ or CD4+ T cells, which are characterized by the capacity of self-renewal and to persist long-term. Once these cells encounter their antigen in vivo, they differentiate further into central memory T cells (TCM), effector memory T cells (TEM) and terminally differentiated effector memory T cells (TEMRA) with some TSCM remaining quiescent (Flynn et al., Clinical & Translational Immunology (2014). These remaining TSCM cells show the capacity to build a durable immunological memory in vivo and therefore are considered an important T cell subpopulation for adoptive T cell therapy (Lugli et al., Nature Protocols 8, 33-42 (2013) Gattinoni et al., Nat. Med. 2011 October; 17(10): 1290-1297). Immune-magnetic selection can be used in order to restrict the T cell pool to the stem cell memory T cell subtype (see Riddell et al. 2014, Cancer Journal 20(2): 141-44)

Antibodies Targeting TCR

Another aspect of the invention refers to an antibody or antigen binding fragment thereof specifically binding to a portion of the TCR as described herein that mediates specificity for MAGEA1. In one embodiment, the portion of the TCR that mediates the MAGEA1 specificity comprises the CDR3 of the alpha chain of SEQ ID NO: 4 and/or the CDR3 of the beta chain of SEQ ID NO: 7.

The antibody or antigen binding fragment thereof may modulate the activity of the TCR. It may block or may not block the binding of the TCR with MAGEA1. It could be used for modulating the therapeutic activity of the TCR or for diagnostic purposes.

Pharmaceutical Compositions, Medical Treatments and Kits

Another aspect of the invention refers to pharmaceutical composition comprising the TCR as described herein, the polypeptide comprising a functional portion of said TCR, the multivalent TCR complex as described herein, the nucleic acid encoding the TCR, the vector comprising said nucleic acid, the cell comprising said TCR, or the antibody specifically binding to a portion of the TCR as described herein.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, PA, latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g. an expanded T cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Typically, the pharmaceutical composition comprises at least one pharmaceutically acceptable carrier.

Accordingly, another aspect of the invention refers to the TCR as described herein, the polypeptide comprising a functional portion of said TCR, the multivalent TCR complex according as described herein, the nucleic acid encoding said TCR, the vector comprising said nucleic acid, the cell comprising said TCR, or the antibody specifically binding to a portion of the TCR as described herein for use as a medicament.

Some embodiments refer to the TCR as described herein, the polypeptide comprising a functional portion of said TCR, the multivalent TCR complex according as described herein, the nucleic acid encoding said TCR, the vector comprising said nucleic acid, the cell comprising said TCR for use in the treatment of cancer.

In one embodiment the cancer is a hematological cancer or a solid tumor.

Hematological cancers also called blood cancers which do not form solid tumors and therefore are dispersed in the body. Examples of hematological cancers are leukemia, lymphoma or multiple myeloma. There are two major types of solid tumors, sarcomas and carcinomas. Sarcomas are for example tumors of the blood vessel, bone, fat tissue, ligament, lymph vessel, muscle or tendon.

In one embodiment, the cancer is selected from the group consisting of prostate cancer, uterine cancer, thyroid cancer, testicular cancer, renal cancer, pancreatic cancer, ovarian cancer, esophageal cancer, non-small-cell lung cancer, lung adenocarcinoma, squamous cell carcinoma, non-Hodgkin's lymphoma, multiple myeloma, melanoma, hepatocellular carcinoma, head and neck cancer, gastric cancer, endometrial cancer, cervical cancer, colorectal cancer, stomach adenocarcinoma, cholangiocarcinoma, breast cancer, bladder cancer, myeloid leukemia and acute lymphoblastic leukemia, sarcoma or osteosarcoma.

Also contemplated herein are pharmaceutical compositions and kits containing one or more of (i) an isolated TCR as described herein; (ii) viral particles comprising a nucleic acid encoding a recombinant TCR; (iii) immune cells, such as T cells or NK cells, modified to express a recombinant TCR as described herein; (iv) nucleic acids encoding a recombinant TCR as described herein. In some embodiments, the present disclosure provides compositions comprising lentiviral vector particles comprising a nucleotide sequence encoding a recombinant TCR described herein (or T cells that have been modified using the vector particles described herein to express a recombinant TCR). Such compositions can be administered to subjects in the methods of the present disclosure as described further herein.

Compositions comprising the modified T cells as described herein can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

The number of cells for an effective treatment in the composition is typically greater than 10 cells, and up to $10^6$, up to and including $10^8$ or $10^9$ cells and can be more than $10^{10}$ cells. The number of cells will depend upon the ultimate use for which the composition is intended as will the type of cells included therein. For uses provided herein, the cells are generally in a volume of a liter or less, can be 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body. In a composition intended to be administered by injection, one or more of a surfactant, preservative, wetting agent, dispersing agent, suspending agent, buffer, stabilizer and isotonic agent may be included.

The recombinant TCRs as described herein, or the viral vector particles comprising a nucleotide sequence encoding a recombinant TCR provided herein, can be packaged as kits. Kits can optionally include one or more components such as instructions for use, devices, and additional reagents, and components, such as tubes, containers and syringes for practice of the methods. Exemplary kits can include the nucleic acids encoding the recombinant TCRs, the recombinant TCR polypeptides, or viruses provided herein, and can optionally include instructions for use, a device for detecting a virus in a subject and a device for administering the compositions to a subject.

Kits comprising polynucleotides encoding a gene of interest (e.g., a recombinant TCR) are also contemplated herein. Kits comprising a viral vector encoding a sequence of interest (e.g., a recombinant TCR) and optionally, a polynucleotide sequence encoding an immune checkpoint inhibitor are also contemplated herein.

Kits contemplated herein also include kits for carrying out the methods for detecting the presence of polynucleotides encoding any one or more of the TCRs disclosed herein. In particular, such diagnostic kits may include sets of appropriate amplification and detection primers and other associated reagents for performing deep sequencing to detect the polynucleotides encoding TCRs disclosed herein. In further embodiments, the kits herein may comprise reagents for detecting the TCRs disclosed herein, such as antibodies or other binding molecules. Diagnostic kits may also contain instructions for determining the presence of the polynucleotides encoding the TCRs disclosed herein or for determining the presence of the TCRs disclosed herein. A kit may also contain instructions. Instructions typically include a tangible expression describing the components included in the kit, and methods for administration, including methods for determining the proper state of the subject, the proper dosage amount, and the proper administration method. Instructions can also include guidance for monitoring the subject over the duration of the treatment time.

Kits provided herein also can include a device for administering a composition described herein to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high-pressure injection device can be included in kits with viruses not damaged by high pressure injection, but is typically not included in kits with viruses damaged by high pressure injection.

Kits provided herein also can include a device for administering a compound, such as a T cell activator or stimulator, or a TLR agonist, such as a TLR4 agonist to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically, the device for administering the compound of the kit will be compatible with the desired method of administration of the compound.

Experiments

1. Experiment: Isolation of MAGEA1-Specific TCRs

To isolate T cells with a specificity for a MAGEA1-derived epitope and a restriction for any MHC molecule of interest, an in vitro priming approach was used. The priming system uses mature dendritic cells (mDCs) of an HLA-A*02:01 negative donor as antigen-presenting cells to initiate an antigen-specific T cell response and expansion of autologous, $CD8^+$ T cells. In vitro transcribed RNA (ivtRNA) encoding a minigene (SEQ ID NO: 27) and being translated into an amino acid sequence containing the MAGEA1-derived peptide KVLEYVIKV (as referenced in SEQ ID NO: 1) serves as the source of specific antigen. Simultaneously, human HLA-A*02:01-encoding ivtRNA was used as the source of the restriction element transfected into mDCs to set-up an allogeneic priming in terms of this dedicated HLA allele (as described in WO2007/017201). After electroporation into mDCs, the minigene-encoding ivtRNA is translated into a protein, which is subsequently processed and presented as peptides by transgenic HLA-A*02:01 molecules which are expressed by co-transfected mDCs. In vitro co-cultures of T cells with the ivtRNA-transfected mDCs from the same donor lead to the de novo induction of antigen-specific T cells that serve as the source of the corresponding TCRs. Following expansion, antigen-specific T cells can be enriched and single-cell cloned by limiting dilution or FACS-based single cell sorting.

1.1 Experimental Layout

The dendritic cell priming of T cells for the isolation and identification of high-affinity TCRs was accomplished by using peptide presentation by allogeneic HLA-A*02:01 molecules according to the following protocol:

Mature dendritic cells were generated within 8 days using suitable maturation cocktails for DCs according to Jonuleit et al. (Jonuleit et al. 1997, Eur. J. Immunol. 1997, 27:3135-3142). The antigen presenting cells (8 day mDCs) were derived from a healthy donor and the cells were transfected by electroporation with 20 µg ivtRNA encoding MG_X1 and with 20 µg ivtRNA coding for the allogeneic HLA molecule (HLA-A*02:01). The prepared mDCs were subsequently co-cultured with autologous $CD8^+$ enriched PBMC of a healthy donor in a ratio of 1:20 for ~14 days in a suitable cell medium supplemented with IL-7 (5 ng/ml at day 0) and IL-2 (50 U/ml every two to three days) at 37° C. (6% $CO_2$). Subsequently, $MAGEA1_{278-286}$-specific cells were identified using an HLA-A*02:01 $MAGEA1_{278-286}$ multimer (ProImmune) and subsequently separated by single cell sorting using FACS technology.

1.2 Results

The described in vitro priming approach resulted in the identification of T cell clones expressing the candidate TCR T15.8-4.3-83. The TCR sequences were identified using NGS analyses, reconstructed and transgenically expressed in suitable effector T cells for a full characterization of the TCR in terms of functionality and safety.

2. Experiment: Epitope Specificity

To assure functionality of the transgenically expressed, recombinant TCR, TCR-transduced effector T cells were co-cultured with peptide-loaded T2 cells (target cells). TCR mediated recognition of a specific peptide:MHC complex leads to the activation of the TCR-expressing T cells and the secretion of certain cytokines, e.g. IFN-γ. To analyze secreted IFN-γ in the co-culture supernatants, an ELISA was performed.

2.2 Experimental Layout

HLA-A*02-expressing T2 cells were loaded with saturating amounts of peptides ($10^{-5}$M). T2 cells loaded with the MAGEA1-derived KVL peptide (SEQ ID NO: 1) served as positive target, T2 cells loaded with an irrelevant ASTN1 peptide (SEQ ID NO 28) served as negative target. As effector cells, CD8-enriched T cell populations from two different donors were transduced to stably express the recombinant TCR T15.8-4.3-83. Effectors were prepared to express two different versions of TCR T15.8-4.3-83, one version with a murine C-region (murC) and one version with a human, minimally murinized C-region (mmC). A control MAGEA1-TCR (benchmark TCR) was also expressed in T cells from two different donors and analyzed.

Effector cells and target cells were co-cultured in an E:T of 2.5:1 in 96-well round-bottom plates. After ~20 h of co-culture, the supernatants were harvested and analyzed by ELISA (standard sandwich ELISA, BD human IFN-γ ELISA set).

2.3 Results

TCR-expressing effector cells only secreted IFN-γ upon cultivation with KVL-peptide-loaded T2 cells, indicating a specific recognition of the presented peptide:MHC complex mediated by the transgenic TCR T15.8-4.3-83 and proving its functionality. The negative target, T2 cells loaded with the irrelevant ASTN1 peptide (SEQ ID NO 28, KLYGLDWAEL), were not recognized (FIG. 1). The transgenic TCR mediates specific target-recognition and secretion of IFN-γ, independent of the TCRs C-region.

3. Experiment: Restriction Analysis

As TCRs recognize their specific epitopes only in combination with a certain MHC molecule, not only the level of antigen-expression but also the HLA-type of a target cell (in vitro and in vivo) defines a target to be a positive or negative target. In other words, dependent on the HLA-type, a patient can or cannot be included into a treatment regimen for TCR-based ACT.

To evaluate, which HLA-molecules, in addition to HLA-A*02:01, can be loaded with the MAGEA1-derived KVL peptide and can be recognized by TCR T15.8-4.3-83-expressing T cells, a detailed restriction analysis was performed. Therefore, 53 LCL cell lines (EBV transformed B cells), covering the most frequent HLA-allotypes in Europeans and North American-Caucasians were used as APC (Antigen Presenting Cell) and co-cultured with TCR-expressing effectors (FIG. 2) either unloaded or loaded with the KVL peptide.

3.1 Experimental Layout:

53 LCL cell lines were loaded with saturating amounts of the MAGEA1-derived KVL peptide ($10^{-5}$ M; SEQ ID NO 1) for ~1.5 h, washed and subsequently co-cultured with TCR T15.8-4.3-83-expressing effectors derived from different effector preparations. Unloaded LCL were used as control. The co-culture was setup with an E:T of 1:1 in 96-well round-bottom plates, supernatants were harvested after ~20 h and levels of IFN-γ were analyzed by ELISA (standard sandwich ELISA, BD human IFN-γ ELISA set).

3.2 Results

The restriction analysis for TCR T15.8-4.3-83 indicates the TCRs potential to recognize its MAGEA1-derived epitope not only presented on HLA-A*02:01 but, in varying degree, also on HLA-A*02:04, HLA-A*02:16, and HLA-A*02:17. FIG. 2 only shows the data for those LCLs (out of 53 tested) that led to a peptide-specific recognition above the background-level detected for the unloaded LCL.

4. Experiment: Tumor Cell Recognition

To analyze the T cell receptor's efficacy, specificity and its suitability for clinical application, a set of tumor cell lines was tested for TCR-mediated recognition by measuring IFN-γ secretion upon co-culture with TCR-transduced effector cells.

4.1 Experimental Layout (FIG. 3):

Effector cells derived from 3 different donors were transduced with TCR T15.8-4.3-83 and benchmark Ctrl. MAGEA1-TCR. Either TCR-transduced or untransduced effectors were co-cultured with different tumor cell lines. Cell lines U266, NCI-H1703, UACC-62, Saos-2 and Mel624.38 (HLA-A2+/MAGEA1+) and HLA-A2-transfected cell lines KYO-1 and OPM-2 (HLA-A2+/MAGEA1+) served as positive-targets. Cell lines NCI-H1755, 647-V and CMK (HLA-A2+/MAGEA1−), unmodified OPM-2 and KYO-1 (HLA-A2−/MAGEA1+) served as negative targets. HLA-A2-expression of the cell lines was analyzed by FACS (data not shown), MAGEA1-expression data were generated using qPCR or extracted from the publicly available databases known to the person skilled in the art. As controls, all effectors were also co-cultured with T2 cells either loaded with saturating concentrations ($10^{-5}$M) of the MAGEA1-derived KVL peptide (SEQ ID NO 1) or with the irrelevant ASTN1-peptide (SEQ ID NO 28). For the co-culture effectors and targets were seeded in 96-well round-bottom plates at an E:T of 2.5:1, supernatants were harvested after ~20 h of co-culture and levels of IFN-γ were analyzed by ELISA.

4.2 Results (FIG. 3):

The TCR's potential to effectively recognize tumor cells was evaluated by co-culturing T15.8-4.3-83-transduced effectors with a set of different tumor cell lines. As shown in FIG. 3, both T15.8-4.3-83 and Ctrl MAGEA1-TCR mediated a specific recognition of HLA-A2-positive and MAGEA1-positive tumor cell lines U266, NCi-H1703, UACC-62, Saos-2 and Mel624.38. KYO-1 and OPM-2 cells were only recognized after transfection with ivtRNA coding for HLA-A2.

Untransfected KYO-1 and OPM-2 (HLA-A2−/MAGEA1-positive) as well as NCI-H1755, 647-V and CMK (HLA-A2+/MAGEA1−) served as negative controls. Whenever the antigen MAGEA1 was not expressed or the restriction element of need was not present, none of the negative controls were recognized. This potent recognition of only MAGEA1-positive and HLA-A2-positive cell lines indicates the TCR's highly effective and specific tumor cell recognition.

4.3 Experimental Layout (FIG. 10)

20.000 TCR-transgenic effector T cells are co-cultured with 20.000 tumor cells in a 96-well round bottom plate. A standard IFN-γ ELISA is performed after 20 h of co-culture with either melanoma cell line UACC-257, melanoma cell line UACC-62 or osteosarcoma cell line SAOS-2. Values above 4000 pg are extrapolated using a third-degree polynomial.

4.5 Results (FIG. 10):

The capacity of TCR-transgenic effector T cell populations to produce IFN-γ in response to MAGEA1 and HLA-A*02:01 double-positive tumor cell lines was evaluated. T15.8-4.3-83 shows enhanced tumor cell recognition capacity for all three cell lines UACC-257, UACC-62 or SAOS-2 compared to the TCRs FH1, FH2, FH3 and FH4 disclosed in WO2018/170338 and R37P1C9 disclosed in WO2018/104438. UACC-62 is only recognized by T15.8-4.3-83.

5. Experiment: Tumor Cell Killing

A TCR's capacity not only to recognize but also efficiently lyse and by this kill tumor cells is of utmost importance and clinical relevance. To analyze the killing capacity of TCR T15.8-4.3-83, an IncuCyte™ Zoom device was used to perform a long-term killing assay over 6 days. The IncuCyte™ device is a microscope-based system that allows live imaging of cells. A set of tumor cell lines was seeded into the wells of a 96-well flat-bottom plate and co-cultured with TCR-expressing effectors derived from 3 different donors. The tumor cell lines were stably expressing the nuclear restricted red fluorescent protein mKate2, enabling the IncuCyte™ Zoom System to determine the exact numbers of red fluorescent cells in each well. An increased cell number per well over time would signify an outgrowth of the tumor cells, while a reduction of the cell number per well would indicate the TCR-mediated killing.

5.1 Experimental Layout (FIGS. 4A-4D)

The tumor cell lines 647-V (bladder urothelial carcinoma), UACC-62 (melanoma), Saos-2 (bone osteosarcoma) and NCI-H1703 (lung adenocarcinoma) were stably transduced with the nuclear restricted red fluorescent protein mKate2 by using the IncuCyte™ NucLight™ Red Lentivirus Reagent according to the manufacturer's instructions. The tumor cells were seeded in 96-well flat-bottom plates to allow attachment to the plastic overnight. As positive control, the tumor cells were loaded with saturating concentrations of the MAGEA1-derived KVL peptide ($10^{-5}$M) for ~1.5 h, washed and then used for the co-culture. The KVL-loaded or unmodified tumor cells were either cultured alone or co-cultured with TCR T15.8-4.3-83-transduced effectors derived from 3 different donors. The co-culture with untransduced effectors served as negative control. The pictures were taken with the IncuCyte™ Zoom System every 2 h and analyzed with the IncuCyte™ Zoom software (Version 2016B).

5.2 Results (FIGS. 4A-4D)

FIGS. 4A-4D show the TCR-mediated, antigen-specific lysis of the red fluorescent target cell lines 647-V (HLA-A2+/MAGEA1−), UACC-62 (HLA-A2+/MAGEA1+), Saos-2 (HLA-A2+/MAGEA1+) and NCI-H1703 (HLA-A2+/MAGEA1+) respectively. While untransduced effector cells do not have an impact on the outgrowth of any of the tumor cells (increasing cell numbers over time), the effector cells transduced with TCR T15.8-4.3-83 efficiently kill the tumor cells NCI-H1703, UACC-62 and Saos-2, which express the antigen MAGEA1 as well as HLA-A2 (decreasing cell numbers over time). MAGEA1− negative 647-V cells are not killed. All tumor cells are killed when they are artificially loaded with the KVL peptide as control. Tumor cells cultured alone, unloaded or loaded with the KVL peptide were also analyzed and the outgrowth is shown in each graph as a reference.

5.3 Experimental Layout (FIG. 11)

20.000 TCR-transgenic effector T cells are co-cultured with 7.500 IncuCyte® NucLight Red Lentivirus-transduced SAOS-2 cells. Tumor cells were seeded one day prior to the start of the co-culture. After addition of effector cells, the culture plates are transferred to an IncuCyte ZOOM® device and expansion of red fluorescent cells is monitored over 72 hours at 37° C. and 6% $CO_2$ with pictures taken every 4 hours. Cell count (1/mm²) of red fluorescent tumor cells per well at every point of measurement are calculated using the IncuCyte ZOOM® software. Each measurement point represents the mean of 3 technical replicates.

5.4 Results (FIG. 11)

SAOS-2 cells cultured in presence of untransduced T cells display a strong proliferation. Co-culture of different TCR-transgenic T cells induces a decrease of SAOS-2 cell numbers. Interestingly, speed and extent of killing varies between different TCR-transgenic effector cells. TCR T15.8-4.3-83 shows the highest capacity to lyse the MAGEA1 and HLA-A*02:01 double-positive tumor cell line compared to the TCRs FH1, FH2, FH3 and FH4 disclosed in WO2018/170338 and R37P1C9 disclosed in WO2018/104438.

6. Experiment: TCR Epitope-Recognition Motif

For the detailed analysis of the TCR's specific epitope-recognition motif, a threonine-substitution scan and/or serine scan was performed. By substitution of the epitope's original amino acids by threonine (or serine respectively), positions within an epitope that are essential for the TCR-mediated recognition can be identified. This recognition depends on proper binding of the peptide to the HLA-molecule and on the interaction of the peptide:MHC-complex with the TCR itself, which can both be affected by the substitution of one single amino acid.

6.1 Experimental Layout (FIGS. 5 and 6)

To specifically define the epitope-recognition motif of TCR T15.8-4.3-8, effectors derived from 3 different donors expressing TCR T15.8-4.3-83 as well as effectors expressing the benchmark MAGEA1-TCR were prepared. The T cells were co-cultured with T2 cells loaded with the TCR's specific epitope KVL (SEQ ID NO 1) or loaded with the peptides having each individual amino acid residue consecutively substituted by threonine (threonine-substitution scan). T2 cells were separately loaded with saturating concentrations ($10^{-5}$M) of the peptides, washed and co-cultured with the effectors at an E:T of 1:1. Supernatants were harvested after ~20 h of co-culture and secreted IFN-γ was analyzed by ELISA.

6.2 Results (FIGS. 5 and 6)

The results of the threonine-substitution scan for effectors transduced with TCR T15.8-4.3-83 (as shown in FIG. 6) or transduced with the benchmark Ctrl. MAGEA1-TCR (as shown in FIG. 5) demonstrate the distinct specificity of the individual TCRs for their epitope and epitope-derived derivatives. As a reference, the recognition of the MAGEA1-derived KVL epitope is shown in each graph on the left. The benchmark Ctrl. MAGE A1-TCR does not recognize peptides with a threonine-substitution at positions 4 and 7 (E and I, FIG. 5). In contrast, TCR T15.8-4.3-83 appears to be highly sensitive for amino-acid-substitutions at positions 1, 3 and 5 (K, L and Y), as indicated by the absent peptide-recognition (FIG. 6).

The exchange of single amino-acids within the epitope markedly interferes with the recognition mediated by both TCRs, proving their highly selective recognition patterns, and the positions that appear critical for the recognition are markedly different for the two analyzed TCRs.

6.3. Experimental Layout (FIG. 13)

20.000 TCR-transgenic T cells are co-cultured with 20.000 $10^{-5}$ M peptide-loaded T2 cells. A standard IFN-γ ELISA is performed after 20 hours of co-culture (values above 4000 pg are extrapolated using a third-degree polynomial). Instead of Threonine residues as described above, serine residues are used to systematically replace individual amino acids in the $MAGEA1_{KVL}$ peptide (Serine Scan).

6.4 Results (FIG. 13)

T cells transduced with the T15.8-4.3-83 TCR display a different recognition motif (according to the serine scan) with different fixed positions than T cells transduced with FH1 or R37P1C9 TCRs.

The combination of both threonine and serine scan indicate that the first position in the epitope (lysine) and the $5^{th}$ position (tyrosine) in the epitope seem to be particular critical for T15.8-4.3-83 TCR.

7 Experiment: MAGE Family Members

As 13 members of the MAGE Family contain peptide sequences highly similar (only 2-4 mismatched amino acids) to the MAGEA1-derived KVL peptide, an in-depth analysis was conducted to further investigate a potential TCR T15.8-4.3-83-mediated cross-recognition. The expression of MAGE Family members is described not only in cancers and testis, but also in vital organs, qualifying a potential cross-recognition of protein-derived peptides to be an exclusion criterion for a TCR for clinical development.

To investigate the recognition of endogenously processed and presented peptides originating from other MAGE family members, all 13 members of the MAGE family containing peptide sequences similar to the MAGEA1-epitope KVLEYVIKV were recombinantly expressed in 3 cell lines of different origin. By co-culturing cell lines, expressing the recombinant MAGE Family Members with TCR T15.8-4.3-83-expressing effectors, the potential cross-recognition of protein-derived MAGE-peptides was analyzed.

7.1 Experimental Layout

IvtRNA encoding the MAGE Family Members MAGEA8 (NCBI Reference Sequence (accession): NM_001166400.1), MAGEA9 (NM_005365.4), MAGEA11 (NM_005366.4), MAGEB1 (NM_002363.4), MAGEB2 (NM_002363.4), MAGEB3 (NM_002365.4), MAGEB5 (NM_001271752.1), MAGEB16 (NM_001099921.1), MAGEB17 (NM_001277307.1), MAGEB18 (NM_173699.3), MAGEC2 (NM_016249.3), MAGED2 (NM_014599.5) and MAGEE2 (NM_138703.4) was produced. IvtRNA encoding for MAGEA1 (NM_004988.4) and the ASTN1 peptide KLY was produced as positive and negative control-RNA. The tumor cell lines HEK 293T (HLA-A2+/MAGE−), LCL (HLA-A2+/MAGE−) and HLA-A2-transduced K562 (MAGE−) were separately transfected with 20 ivtRNA encoding either one of the 13 MAGE Family Members, MAGEA1 or the ASTN1 peptide KLY. The transgenic expression of the MAGE Family Members was analyzed by FACS (data not shown). As control, T2 cells as well as the 3 cell lines were additionally loaded with either the MAGEA1-derived KVL peptide ($10^{-5}$M) or the ASTN1-derived KLY peptide ($10^{-5}$M). The peptide-loaded control cells and the transfected cell lines were seeded 3 h after transfection into 96-well round-bottom plates and co-cultured with untransduced or TCR T15.8-4.3-83-transduced effectors derived from 2 donors at an E:T ratio of 1:1. Supernatants were harvested after ~20 h of co-culture and secreted IFN-γ was analyzed by ELISA.

7.2 Results

FIG. 7 shows the TCR T15.8-4.3-83-mediated recognition of the recombinant MAGE Family Members expressed in HEK 293T cells (A), K562 cells (B) and LCL cells (C). The recognition of T2 cells as well as HEK 293T, K562 or LCL cells externally loaded with the KVL peptide or the ASTN1 peptide served as controls. While untransduced effectors did not show any specific recognition, TCR T15.8-4.3-83 transduced effectors derived from 2 donors specifically recognized all 3 cell lines transfected with the full length MAGEA1-encoding ivtRNA. This indicates the efficient translation of the MAGEA1-encoding RNA into MAGEA1 protein and the proteosomal processing of the protein-derived KVL peptide followed by the loading and presentation of the epitope by HLA-A2 molecules on the cell surface. There was no recognition of any of the cell lines either transfected with the ASTN1 peptide as well as no recognition of any of the recombinantly expressed MAGE Family Members above background levels. The MAGE Family Member-derived peptides, that can be recognized upon artificial loading of target cells (as described before), are either not processed from the endogenously expressed MAGE proteins, not loaded onto the WIC molecules or not presented on the cell surface. Therefore, these peptides are not qualified as immunogenic T cell epitopes and are not considered to be clinically relevant targets for a TCR T15.8-4.3-83-mediated cross-recognition.

8. Experiment: Normal Cell Analyses

To investigate a TCR's safety profile, the TCR-mediated recognition of cells derived from healthy tissues of different origin has to be investigated and excluded. Therefore, TCR-expressing effectors were co-cultured with normal cells derived from the kidney (renal cortical epithelial cells obtained by PromoCell), lung (lung fibroblasts obtained by Lonza), and iPS-derived hepatocytes, cardiomyocytes, and endothelial cells (obtained by Cellular Dynamics). The investigated cells were endogenously negative for the antigen MAGEA1 and therefore allowed the identification of potential MAGEA1-unrelated off-target toxicities.

8.1 Experimental Layout

The normal cells were thawed and cultivated for one week prior the co-culture as specified by the suppliers. The cells were seeded in 96-well flat-bottom plates and co-cultured with TCR T15.8-4.3-83-transduced or untransduced effectors (data not shown) derived from 3 different donors. HLA-A2-expression of the target cells was confirmed by antibody-staining and FACS (data not shown) and the target cells were either tested unmodified or loaded with exceeding amounts ($10^{-5}$M) of the MAGEA1-derived KVL (SEQ ID NO 1) peptide as a control. As controls, effector cells and target cells were seeded alone, and T2 cells were loaded with the TCR's epitope KVL ($10^{-5}$ M; SEQ ID NO 1). After ~20 h of co-culture, supernatants were harvested and analyzed by ELISA. After ~48 h of co-culture, phase-contrast images were taken with an IncuCyte™ Zoom device (Essen BioScience Inc.) to visualize potential toxic effects in terms of lysis and detachment of the adherent target cells.

8.2 Results

As shown in FIG. 8, co-culturing of TCR T15.8-4.3-83-transduced effectors derived from 3 donors resulted in the recognition of only artificially KVL peptide-loaded cells, representing the target cells potential to properly present the TCR's epitope on their cell surface in the context of MHC molecules. The unmodified normal cells were not recognized by effectors expressing the transgenic TCR T15.8-4.3-83, indicating a favorable safety profile of the investigated receptor.

To visualize potential toxic effects mediated by the TCR-transduced effectors on the target cells, phase-contrast images were taken of the different target cells either cultured alone, co-cultured with TCR T15.8-4.3-83-transduced effectors or of KVL peptide-loaded target cells co-cultured with TCR-expressing effectors. FIG. 9 shows representative pictures of co-cultures with effector cells from one of the three donors. While there is a clear TCR-mediated lysis of all KVL-loaded target cells (complete disruption of the cell layer), the TCR-expressing effector cells do not lyze unmodified normal cells.

9 Experiment: Functional Avidity

To measure functional avidity of different KVL peptide-specific TCRs the half-maximal relative IFN-γ release (EC50 value) in co-culture with T2 cells loaded with graded amounts of KVL peptide is determined.

Functional avidity refers to the accumulated strength of multiple affinities of individual non-covalent binding interactions between the transgenic TCR and the pMHC complex.

9.1 Experimental Layout (FIG. 12)

Functional avidities of TCR-transgenic T cell populations are determined as the half-maximal relative IFN-γ release (EC50 values) in co-culture with T2 cells loaded with graded amounts of KVL peptide ($10^{-4}$ M to $10^{-12}$M). A standard IFN-γ ELISA is performed after 20 h of co-culture (values above 4000 pg are extrapolated using a third-degree polynomial.

9.2 Results (FIG. 12)

Different KVL-specific TCRs differ in their functional avidities T2 cells loaded with KVL peptide. TCR T15.8-4.3-83 shows a low EC50 value, i.e. a high functional avidity to 2 cells loaded with KVL peptide compared to the TCRs FH1, FH2, FH3 and FH4 disclosed in WO2018/170338 and R37P1C9 disclosed in WO2018/104438.

10 Experiment: Cytokine Secretion

TCRs secretion pattern of the TH2 specific cytokines IL-4, IL-5 and IL-13 of T cells transduced with different TCRs is compared. Th2-type inflammation has been proposed to facilitate tumor growth (Jager M J, Desjardins L, Kivelä T, Damato BE (eds): Current Concepts in Uveal Melanoma. Dev Ophthalmol. Basel, Karger, 2012, vol 49, pp 137-149, J Immunother. 2018 October; 41(8):369-378). Hence, the low or non-detectable secretion levels Th2 may be advantageous for tumor regression.

10.1 Experimental Layout (FIG. 14)

20.000 TCR-transgenic effector T cells are co-cultured with 20.000 tumor cells in a round bottom 96-well plate. Cell-free supernatant was analyzed regarding secreted cytokines using a MILLIPPLEX® MAP Kit according to protocol in a MAGPIX® system.

10.2 Results (FIG. 14)

T cells transduced with the T1367 TCR secrete several TH2 cytokines, especially IL-4, IL-5 and IL-13. T cells transduced with the 15.8-4.3-83 TCR do not display an equivalent secretion of TH2-cytokines while T1367 disclosed in WO2014/118236 shows significant secretion of these cytokines.

The application further comprises the following embodiments:

Embodiment 1: Isolated T cell receptor (TCR) specific for MAGEA1.

Embodiment 2: Isolated TCR according to embodiment 1, wherein the TCR specifically recognizes the amino acid sequence SEQ ID NO: 1 or a fragment thereof.

Embodiment 3: Isolated TCR according to embodiments 1 and 2, wherein the TCR specifically recognizes the HLA-A2 and/or HLA-A26 bound form of the amino acid sequence of SEQ ID NO: 1, preferably the HLA-A2 bound form.

Embodiment 4: Isolated TCR according to any of the preceding embodiments, wherein the TCR specifically recognizes the amino acid sequence of SEQ ID NO: 1, which is presented by a molecule encoded by a gene selected from the group consisting of HLA-A*02:01, HLA-HLA-A*02: 04, HLA-A*02:16 and HLA-A*02:17.

Embodiment 5: Isolated TCR according to any of the preceding embodiments, wherein the TCR specifically recognizes the amino acid sequence of SEQ ID NO: 1, which is presented by a molecule encoded by a gene selected from the group consisting of HLA-A*02:01, HLA-A*02:04, HLA-A*02:16 and HLA-A*02:17.

Embodiment 6: Isolated TCR according to any of the preceding embodiments, wherein the TCR specifically recognizes the amino acid sequence of SEQ ID NO: 1, which is presented by the HLA-A*02:01 encoded molecule.

Embodiment 7: Isolated TCR according to any one of the preceding embodiments, wherein the TCR comprises
- a TCR α chain comprising a CDR1 having the amino acid sequence of SEQ ID NO: 2, a CDR2 having the amino acid sequence of SEQ ID NO: 3 and a CDR3 having the amino acid sequence of SEQ ID NO: 4,
- a TCR β chain comprising a CDR1 having the amino acid sequence of SEQ ID NO: 5, a CDR2 having the amino acid sequence of SEQ ID NO: 6 and a CDR3 having the amino acid sequence of SEQ ID NO: 7.

Embodiment 8: Isolated TCR according to any one of the preceding embodiments, wherein the TCR comprises a variable TCR α region having an amino acid sequence which is at least 80% identical to SEQ ID NO: 8 and a variable TCR β region having an amino acid sequence which is at least 80% identical to SEQ ID NO: 9.

Embodiment 9: Isolated TCR according to any one of the preceding embodiments, wherein the TCR comprises a variable TCR α region having the amino acid sequence of SEQ ID NO: 8 and a variable TCR β region having the amino acid sequence of SEQ ID NO: 9.

Embodiment 10: Isolated TCR according to any one of the preceding embodiments, wherein the TCR comprises a TCR α chain having an amino acid sequence which is at least 80% identical to SEQ ID NO: 10 and a TCR β chain having an amino acid sequence which is at least 80% identical to SEQ ID NO: 11.

Embodiment 11: Isolated TCR according to any one of the preceding embodiments, wherein the TCR comprises a TCR α chain having the amino acid sequence of SEQ ID NO: 10 or SEQ ID NO: 12 and a TCR β chain having the amino acid sequence of SEQ ID NO: 11 or SEQ ID NO: 13.

Embodiment 12: Isolated TCR according to any one of the preceding embodiments, wherein the TCR comprises a TCR α chain and a TCR β chain, wherein
- the variable TCR α region has an amino acid sequence which is at least 80% identical to SEQ ID NO: 8 and comprises a CDR3 having the amino acid sequence set out in SEQ ID NO: 4,
- the variable TCR β region has an amino acid sequence which is at least 80% identical to SEQ ID NO: 9 and comprises a CDR3 having the amino acid sequence set out in SEQ ID NO: 7.

Embodiment 13: Isolated TCR according to any one of the preceding embodiments, wherein the TCR is purified.

Embodiment 14: Isolated TCR according to any one of the preceding embodiments, wherein its amino acid sequence comprises one or more phenotypically silent substitutions.

Embodiment 15: Isolated TCR according to any one of the preceding embodiments, wherein its amino acid sequence is modified to comprise a detectable label, a therapeutic agent or pharmacokinetic modifying moiety.

Embodiment 16: Isolated TCR according to embodiment 15, wherein the therapeutic agent is selected from the group consisting of an immune effector molecule, a cytotoxic agent and a radionuclide.

Embodiment 17: Isolated TCR according to embodiment 16, wherein the immune effector molecule is a cytokine.

Embodiment 18: Isolated TCR according to any one of the preceding embodiments, wherein the TCR is soluble or membrane bound.

Embodiment 19: Isolated TCR according to embodiment 15, wherein the pharmacokinetic modifying moiety is at least one polyethylene glycol repeating unit, at least one glycol group, at least one sialyl group or a combination thereof.

Embodiment 20: Isolated TCR according to any one of the preceding embodiments, wherein the TCR is of the single chain type, wherein the TCR α chain and the TCR β chain are linked by a linker sequence.

Embodiment 21: Isolated TCR according to embodiments 1 to 20, wherein the TCR α chain or the TCR β chain is modified to comprise an epitope tag.

Embodiment 22: Isolated polypeptide comprising a functional portion of the TCR of any of embodiments 1 to 21, wherein the functional portion comprises at least one of the amino acid sequences of SEQ ID NOs: 4 and 7.

Embodiment 23: Isolated polypeptide comprising a functional portion of the TCR of any of embodiments 1 to 21, wherein the functional portion comprises the amino acid sequences of SEQ ID NOs: 2, 3, 4, 5, 6, and 7.

Embodiment 24: Isolated polypeptide according to embodiment 21, wherein the functional portion comprises the TCR α variable chain and/or the TCR β variable chain.

Embodiment 25: Multivalent TCR complex comprising the TCR as embodied in any one of embodiments 1 to 21.

Embodiment 26: Isolated TCR according to embodiments 1 to 21, polypeptide according to embodiments 22 to 24, multivalent TCR complex according to embodiment 25, wherein IFN-γ secretion is induced by binding to the amino acid sequence of SEQ ID NO: 1, which is presented by the HLA-A*02:01 encoded molecule.

Embodiment 27: Nucleic acid encoding a TCR according to any one of embodiments 1 to 21 or encoding the polypeptide according to embodiments 22 to 24.

Embodiment 28: Vector comprising the nucleic acid of embodiment 27.

Embodiment 29: Vector according to embodiment 28, wherein the vector is an expression vector.

Embodiment 30: Vector according to embodiment 28 or 29, wherein the vector is a retroviral vector.

Embodiment 31: Vector according to embodiment 28 or 29, wherein the vector is a lentiviral vector.

Embodiment 32: Cell expressing the TCR according to embodiments 1 to 21.

Embodiment 33: Cell according to embodiment 32, wherein the cell is isolated or non-naturally occurring.

Embodiment 34: Cell according to embodiments 32 and 33, wherein the cell comprises the nucleic acid according to embodiment 27 or the vector according to embodiments 28 to 31.

Embodiment 35: Cell according to embodiments 32 to 34, wherein the cell comprises:
a) an expression vector which comprises at least one nucleic acid as embodied in embodiment 27, or
b) a first expression vector which comprises a nucleic acid encoding the alpha chain of the TCR as embodied in any one of the embodiments 1 to 21, and a second expression vector which comprises a nucleic acid encoding the beta chain of a TCR as embodied in any one of the embodiments 1 to 21.

Embodiment 36: Cell according to any one of embodiments 32 to 35, wherein the cell is a peripheral blood lymphocyte (PBL) or a peripheral blood mononuclear cell (PBMC).

Embodiment 37: Cell according to any one of embodiments 32 to 36, wherein the cell is a T cell.

Embodiment 38: Antibody or antigen binding fragment thereof specifically binding to a portion of the TCR according to embodiments 1 to 21 that mediates specificity for MAGEA1.

Embodiment 39: Antibody according to embodiment 38, wherein the portion of the TCR that mediates the MAGEA1 specificity comprises at least one of the CDRs set out in SEQ ID NOs: 2, 3, 4, 5, 6, and 7, preferably the CDR3 of the alpha chain of SEQ ID NO: 4 and/or the CDR3 of the beta chain of SEQ ID NO: 7, more preferably the CDRs of the alpha chain set out in SEQ ID NOs: 2, 3 and 4, and the CDRs of the beta chain of SEQ ID 5, 6 and 7.

Embodiment 40: Pharmaceutical composition comprising the TCR according to embodiments 1 to 21, the polypeptide according to embodiments 22 to 24, the multivalent TCR complex according to embodiment 25 the nucleic acid according to embodiment 27, the vector according to embodiments 28 to 31, the cell according to any one of embodiments 32 to 37, or the antibody according to embodiments 38 to 39.

Embodiment 41: Pharmaceutical composition according to embodiment 40 wherein the pharmaceutical composition comprises at least one pharmaceutically acceptable carrier.

Embodiment 42: The TCR according to embodiments 1 to 21, the polypeptide according to embodiments 22 to 24, the multivalent TCR complex according to embodiment 25, the nucleic acid according to embodiment 27, the vector according to embodiments 28 to 31, the cell according to any one of embodiments 32 to 37, or the antibody according to embodiments 38 to 39 for use as a medicament.

Embodiment 43: The TCR according to embodiments 1 to 21, the polypeptide according to embodiments 22 to 24, the multivalent TCR complex according embodiment 25, the nucleic acid according to embodiment 27, the vector according to claims 28 to 31 or the cell according to any one of embodiments 32 to 37 for use in the treatment of cancer.

Embodiment 44: The TCR, the polypeptide, the multivalent TCR complex, the nucleic acid, the vector or the cell according to embodiment 43, wherein the cancer is a hematological cancer or a solid tumor.

Embodiment 45: The TCR, the polypeptide, the multivalent TCR complex, the nucleic acid, the vector or the cell according to embodiments 43 and 44, wherein the cancer is selected from the group consisting of prostate cancer, uterine cancer, thyroid cancer, testicular cancer, renal cancer, pancreatic cancer, ovarian cancer, esophageal cancer, non-small-cell lung cancer, lung adenocarcinoma, squamous cell carcinoma, non-Hodgkin's lymphoma, multiple myeloma, melanoma, hepatocellular carcinoma, head and neck cancer, gastric cancer, endometrial cancer, cervical cancer, colorectal cancer, stomach adenocarcinoma, cholangiocarcinoma, breast cancer, bladder cancer, myeloid leukemia and acute lymphoblastic leukemia, sarcoma or osteosarcoma.

Embodiment 46: The TCR, the polypeptide, the multivalent TCR complex, the nucleic acid, the vector or the cell according to embodiments 43 and 44, wherein the cancer is preferably selected from the group consisting sarcoma or osteosarcoma.

The invention claimed is:

1. An isolated T cell receptor (TCR) specific for Melanoma-Associated Antigen 1 (MAGEA1), wherein the TCR comprises
a TCR α chain comprising
a CDR1 having the amino acid sequence of SEQ ID NO: 2,
a CDR2 having the amino acid sequence of SEQ ID NO: 3 and
a CDR3 having the amino acid sequence of SEQ ID NO: 4;
and
a TCR β chain comprising
a CDR1 having the amino acid sequence of SEQ ID NO: 5,
a CDR2 having the amino acid sequence of SEQ ID NO: 6 and
a CDR3 having the amino acid sequence of SEQ ID NO: 7.

2. The isolated TCR according to claim 1, wherein the TCR comprises
a variable TCR α region having an amino acid sequence which is at least 85% identical to SEQ ID NO:8 and
a variable TCR β region having an amino acid sequence which is at least 80% identical to SEQ ID NO: 9.

3. A nucleic acid encoding a TCR according to claim 1.

4. A vector comprising the nucleic acid of claim 3.

5. The vector of claim 4, wherein the vector is an expression vector.

6. The vector of claim 4, wherein the vector is a retroviral vector or a lentiviral vector.

7. A cell expressing the TCR according to claim 1.

8. A pharmaceutical composition comprising the isolated TCR according to claim 1.

9. A composition comprising the nucleic acid according to claim 3.

* * * * *